(12) United States Patent
Olek

(10) Patent No.: US 9,840,736 B2
(45) Date of Patent: Dec. 12, 2017

(54) EPIGENETIC MARKER FOR THE IDENTIFICATION OF T LYMPHOCYTES

(75) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 482 days.

(21) Appl. No.: 13/575,819

(22) PCT Filed: Feb. 3, 2011

(86) PCT No.: PCT/EP2011/051601
§ 371 (c)(1),
(2), (4) Date: Sep. 18, 2012

(87) PCT Pub. No.: WO2011/095564
PCT Pub. Date: Aug. 11, 2011

(65) Prior Publication Data
US 2013/0005600 A1    Jan. 3, 2013

(30) Foreign Application Priority Data
Feb. 3, 2010 (EP) .................................. 10001121

(51) Int. Cl.
*C12Q 1/68* (2006.01)
*G01N 33/68* (2006.01)
*G01N 33/569* (2006.01)

(52) U.S. Cl.
CPC ..... *C12Q 1/6881* (2013.01); *G01N 33/56966* (2013.01); *G01N 33/6875* (2013.01); *C12Q 2600/154* (2013.01)

(58) Field of Classification Search
CPC ................ C12Q 1/6827; C12Q 1/6858; C12Q 2600/154; C12Q 2537/164; C12Q 2521/331; C12Q 2831/113; C12Q 2545/113; C12Q 1/6881
See application file for complete search history.

(56) References Cited

FOREIGN PATENT DOCUMENTS

| EP | 1 748 080 A2 | 1/2007 |
| EP | 2 248 913 A1 | 11/2010 |
| WO | WO 2008084219 A1 * | 7/2008 |

OTHER PUBLICATIONS

Wieczorek et al. Quantitative DNA methylation analysis of FOXP3 as a new method for counting regulatory T cells in peripheral bloood and solid tissue. Cancer Research, vol. 69, pp. 599-608, 2009.*
Hoque et al. Quantitation of promoter methylation of multiple genes in urine DNA and bladder cancer detection. Journal of the National Cancer Institute, vol. 98, No. 14, pp. 996-1004, Jul. 2006.*
Oestreich et al. NFATc1 regulates PD-1 expression upon T cell activation. The Journal of Immunology, vol. 181, pp. 4832-4839, 2008.*
Takashi et al. Interleukin-1 induced maturation of progenitor thymocytes. European Journal of Immunology, vol. 21, pp. 1385-1390, 1991.*
Flanagan et al. DNase hypersensitivity and methylation of the human CD3G and D genes during T-cell development. Immunogenetics, vol. 31, pp. 13-20, 1990.*
Javierre et al. Changes in the pattern of DNA methylation associate with twin discordance in systemic lupus erythematosus. Genome Research, vol. 20, pp. 170-179, 2010.*
Korshunova et al. Massivly parallel bisulphite pyrosequencing reveals the molecular complexity of breast cancer-associated cytosine-methylation patterns obtained from tissue and serum DNA. Genome Research, vol. 18, No. 1, pp. 19-29, Nov. 2007.*
Brunner et al. Distinct DNA methylation patterns characterize differentiated human embryonic stem cells and developing human fetal liver. Genome Research, vol. 19, No. 6, pp. 1044-1056, Jun. 2009.*
Sehouli et al. Epigenetic quantification of tumor-infiltrating T-lymphocytes. Epigenetics, vol. 6, No. 2, pp. 236-246, Feb. 2011.*
Baron, Udo et al., "DNA demethylation in the human FOXP3 locus discriminates regulatory T cells from activated FOXP3+conventional T cells," *European Journal of Immunology*, Sep. 1, 2007, vol. 37, No. 9, pp. 2378-2389.
Baron, Udo et al., "DNA methylation analysis as a tool for cell typing," *Epigenetics: Official Journal of the DNA Methylation Society*, Jan. 2006, vol. 1, No. 1, pp. 55-60.
Du, XinLi et al., "Genomic profiles for human peripheral blood T cells, B cells, natural killer cells, monocytes, and polymorphonuclear cells: Comparisons to ischemic stroke, migraine, and Tourette syndrome," *Genomics*, Jun. 1, 2006, vol. 87, No. 6, pp. 693-703 (available on line Mar. 20, 2006).
Kishi, Atsuko et al., "Differential expression of granulysin and perforin by NK cells in cancer patients and correlation of impaired granulysin expression with progression of cancer," *Cancer Immunology and Immunotherapy*, Jan. 1, 2002, vol. 50, No. 11, pp. 604-614.
Meyer, Kurt. et al., "Direct effect of cocaine on epigenetic regulation of PKCε gene repression in the fetal rat heart," *Journal of Molecular and Cellular Cardiology*, Oct. 1, 2009, vol. 47, No. 4, pp. 504-511.
Slagboom, P.Eline. etal., "Messenger RNA levels and methylation patterns of GAPDH and β-actin genes in rat liver, spleen and brain in relation to aging," *Mechanisms of Ageing and Development*, Apr. 30, 1990, vol. 53, No. 3, pp. 243-257.

* cited by examiner

*Primary Examiner* — Jennifer Dunston
(74) *Attorney, Agent, or Firm* — Saliwanchik, Lloyd & Eisenschenk

(57) ABSTRACT

The invention relates to a method for identifying a specific type and/or state of a mammalian cell in a sample, the method comprising a) analyzing the relative amount of accessible chromatin in regions that are specific for a cell-type and/or cellular state in the genome of the cell, b) comparing the relative amount of accessible chromatin in the regions with the relative amount of accessible chromatin in regions in the genome of the cell that are unspecific for the cell-type and/or cellular state, and c) deducing the specific type and/or state of said mammalian cell in the sample based on such comparison. The identifying further comprises a relative quantification of the specific cell type and/or state. The method can further comprise a diagnosis of a predisposition to a disease or a disease based on such identification. Kits and markers in regions of accessible chromatin are also described.

5 Claims, 12 Drawing Sheets

SEQUENCE LISTING

```
<160> NUMBER OF SEQ ID NOS: 29

<210> SEQ ID NO 1
<211> LENGTH: 630
<212> TYPE: DNA
<213> ORGANISM: Artificial Sequence
<220> FEATURE:
<223> OTHER INFORMATION: Plasmid insert containing methylation segments

<400> SEQUENCE: 1
gcggccgccc taaacactac cacatctcaa aaccccttaa aaaaaaccat caacccata       60 acacaaacca taacaactaa atttctgatc gtttttgatt tgtttagatt tttttgttat     120
tgatgttatg gtggttggat gtgttgggtt ttattgatat tatggaggaa gagaagaggc    180
tcgacccaaa cccctacctc cacatctaca taataaaaac cattaacccct catcaataaa   240 tctacatttc ctcaaaccta cactatctaa aattatacaa aactaataaa aaaacaaaat    300
ctcttctata ttcagtcgga atagaggaga agagagagtt tcattttttt ggttttttag    360
aaggaacatg agaatacatg tttgtgttga gagtgggtta gagcagtttt agggtaaagt    420
atgtggataa gtcggttttt ggtattgtag gttttgggat gttagtgtgt agtgggtgta    480
tttttgtttg gatgttgtgt ttgtggtaga gtggttgtta tgttgtaatt ggagtcgttt    540
tttttaaaga gtgtttttga tagggattgt tttaggaatt aggtaggaga gaagggagtg   600
tgagaggtga aagttattat tattctcgag                                     630

<210> SEQ ID NO 2
```

```
<211> LENGTH: 22
<212> TYPE: DNA
<213> ORGANISM: Artificial Sequence
<220> FEATURE:
<223> OTHER INFORMATION: bisulfite converted

<400> SEQUENCE: 2
cttctctaaa cccaacatca at                                              22

<210> SEQ ID NO 3
<211> LENGTH: 22
<212> TYPE: DNA
<213> ORGANISM: Artificial Sequence
<220> FEATURE:
<223> OTHER INFORMATION: bisulfite converted

<400> SEQUENCE: 3
gaatttagga ggtagaggtg gt                                              22

<210> SEQ ID NO 4
<211> LENGTH: 22
<212> TYPE: DNA
<213> ORGANISM: Artificial Sequence
<220> FEATURE:
<223> OTHER INFORMATION: bisulfite converted

<400> SEQUENCE: 4
ggatatttga tttgggagtt ta                                              22

<210> SEQ ID NO 5
<211> LENGTH: 24
<212> TYPE: DNA
<213> ORGANISM: Artificial Sequence
<220> FEATURE:
<223> OTHER INFORMATION: bisulfite converted

<400> SEQUENCE: 5
aaccactaac aacttctatt ttca                                            24

<210> SEQ ID NO 6
<211> LENGTH: 24
<212> TYPE: DNA
<213> ORGANISM: Artificial Sequence
<220> FEATURE:
<223> OTHER INFORMATION: bisulfite converted

<400> SEQUENCE: 6
ttttgtgtta atatgaggtt gttt                                            24

<210> SEQ ID NO 7
<211> LENGTH: 22
<212> TYPE: DNA
<213> ORGANISM: Artificial Sequence
<220> FEATURE:
<223> OTHER INFORMATION: bisulfite converted

<400> SEQUENCE: 7
accctctccc tactcaaata ct                                              22

<210> SEQ ID NO 8
<211> LENGTH: 25
<212> TYPE: DNA
<213> ORGANISM: Artificial Sequence
<220> FEATURE:
<223> OTHER INFORMATION: bisulfite converted

<400> SEQUENCE: 8
```

```
agtggtataa ttttgttttg atttt                                          25

<210> SEQ ID NO 9
<211> LENGTH: 21
<212> TYPE: DNA
<213> ORGANISM: Artificial Sequence
<220> FEATURE:
<223> OTHER INFORMATION: bisulfite converted

<400> SEQUENCE: 9
aaattctcat cctcccacta a                                              21

<210> SEQ ID NO 10
<211> LENGTH: 22
<212> TYPE: DNA
<213> ORGANISM: Artificial Sequence
<220> FEATURE:
<223> OTHER INFORMATION: bisulfite converted

<400> SEQUENCE: 10
acccacaaac ctacattaaa aa                                             22

<210> SEQ ID NO 11
<211> LENGTH: 22
<212> TYPE: DNA
<213> ORGANISM: Artificial Sequence
<220> FEATURE:
<223> OTHER INFORMATION: bisulfite converted

<400> SEQUENCE: 11
gtaaggagag tgatgaggaa aa                                             22

<210> SEQ ID NO 12
<211> LENGTH: 22
<212> TYPE: DNA
<213> ORGANISM: Artificial Sequence
<220> FEATURE:
<223> OTHER INFORMATION: bisulfite converted

<400> SEQUENCE: 12
caattcacaa atcccataaa ta                                             22

<210> SEQ ID NO 13
<211> LENGTH: 22
<212> TYPE: DNA
<213> ORGANISM: Artificial Sequence
<220> FEATURE:
<223> OTHER INFORMATION: bisulfite converted

<400> SEQUENCE: 13
ttgtttaggt gaggataggt tt                                             22

<210> SEQ ID NO 14
<211> LENGTH: 22
<212> TYPE: DNA
<213> ORGANISM: Artificial Sequence
<220> FEATURE:
<223> OTHER INFORMATION: bisulfite converted

<400> SEQUENCE: 14
aggtatttta agggtttgaa tg                                             22

<210> SEQ ID NO 15
<211> LENGTH: 22
<212> TYPE: DNA
```

<213> ORGANISM: Artificial Sequence
<220> FEATURE:
<223> OTHER INFORMATION: bisulfite converted

<400> SEQUENCE: 15
tctcctcaca atctaacaaa aa                                          22

<210> SEQ ID NO 16
<211> LENGTH: 455
<212> TYPE: DNA
<213> ORGANISM: Homo sapiens

<400> SEQUENCE: 16
gaacccagga ggcagaggtg gcagtgagcc gagaccgtgc cattgcactc cagcctgggt    60
gacagagcga gactccgtct taaaaaataa ataaaaacagg gtaaaaacac agaagttaca   120
gaagcctggc aggaaaagcc aaagacagaa ggctgacgga ggctttaaac gcacttcgtt   180
gacattcagg accctcggga atattcctcg ccctacggg ggtggggtg tgcttgttct    240 tattttggtc tcacatcctt tcaggccag ccttcctcct cctgcatggc caagcaggg    300 gagtccttcc ttgggaggcc gcctgttctc tccccgcctc ctggttctgg atttgggtag   360
ggcaggattt gggtgttcac cctcctagga ggccctgaga ggctgccagg ccccagctct   420
gcttcctcca cccactgatg ctgggctcag agaag                               455

<210> SEQ ID NO 17
<211> LENGTH: 427
<212> TYPE: DNA
<213> ORGANISM: Homo sapiens

<400> SEQUENCE: 17
agccactgac agcttctatt ttcatagacc taaatatggg cttgccaccc ggataacatt    60
acacgcatgg cctctcctgg tgctccccac acccgggtga agtccgtgtt attattatct   120
ccatttctca ggtaagagaa ttgggtgaga actagagatg ttaagcagca agttcccaca   180
gggctgaagg aggtgagtgg tagcgtcaag atgtgaacca ctgttactgc acactgaatc   240
ataccactat ggccgatcac agagggccct ggggagccac ggaaggctct aggcagaggc   300
agggcctctt gggttagaag gacggcctgg agttgggatc ctgccacccg gcacttacca   360
gcagacaccc caccatgaga ttatgtctct tgatgattga gcaaataggc tcccaggtca   420
aatgtcc                                                             427

<210> SEQ ID NO 18
<211> LENGTH: 458
<212> TYPE: DNA
<213> ORGANISM: Homo sapiens

<400> SEQUENCE: 18
accctctccc tgctcagatg ctcccgcctc cctgcctttt atgccagggt gggtccgttc    60
cttggctggg cttccagggc atttcaggat ctgtccctct tgcctctgag ccccttgacc   120
gccgacccca ccgcagctct cagccctctg cctgccacgc cttcccctc ttccccagcc   180 cccgctgagt ccagcactgc cggcctggct cacctgcagg aagcctggta gctccttctc   240
catcagcacc ttgagctccc ccttggtcag ggtctgcgtg ctgccctcgc tgcccgaata   300
tcgggaaaag acgtctatga tcatgcccat ggctgtctct agttccgtca tggtgctaga   360
ttcagaccca ccttcctcct gggggctggc agggccgaga aaatgtccca ctggcagcct   420
cttggtgctt tataaggcag cctcatattg acacagag                           458

```
<210> SEQ ID NO 19
<211> LENGTH: 379
<212> TYPE: DNA
<213> ORGANISM: Homo sapiens

<400> SEQUENCE: 19
aaattctcat cctcccacta agggtagtgc ttttcagaca aagataccat ttaatagacc      60
tcgaggacac aacttttcat tgcagacaag tgctgttgtt ttgaaaaaca ctgcaggtgc     120
tacaaaggtc atagcagctc aggcacagca agctcacgtg caggcacctc agattggggc    180
gtggcgaaac agattgcatt tcctagaagg cccccagcga tgtggattga agcgcaagag   240
tgaggagttg ataatcata gcagcgcaat gcagattgtc gatgaattgt ccatacttcc    300
tgcaatgttg caaaccaaca tgggaaatcc agtgacagtt gtgacagcta ccacaggatc    360
aaaacagaat tgtaccact                                                  379

<210> SEQ ID NO 20
<211> LENGTH: 308
<212> TYPE: DNA
<213> ORGANISM: Homo sapiens

<400> SEQUENCE: 20
gtaaggagag tgatgaggaa aaaggggtgg ctgccctgct cggtgctgtt ctgtcaaaga     60
gccgaaattc ttcgcggggt ggcagatgag gacaggaaca gctgggtgt ggcaagtgtt    120 gctgcctggg gagagcggag ggtgaggtgt ttctcacggg tgcatccagt gactcatcag    180
gacagcggag ctcatgaggc catgtctccc gtttcctgcc ttagaatcac atgaaaatga    240
gcagagggtg ggtcatcagg acagggctct ccggggagcg aagcgccctt caatgcaggc    300
ctgtgggc                                                             308

<210> SEQ ID NO 21
<211> LENGTH: 388
<212> TYPE: DNA
<213> ORGANISM: Homo sapiens

<400> SEQUENCE: 21
ctgctcaggt gaggacaggc ttctcatgag gtccctgaga aacttgcctt ttggagggaa      60
atgtcctctg ccctctggag cctggggaga aggttatttc tgcccgccag accagcatgc    120
tcgcttttct tccatgggca ttcaggaatc ctggccccat tctgacattc ctcaaatgga    180
ggaattcctc aaattaccag aggaaagtta ccaaagttta gatctgctgg agctcttcaa    240
ggattggcct gagacaagcc gggaggtgcc acggggcttg gagctggccc tgtgaggcac    300
ctccggggga agttcatgtc ctaggtggtt cacgtcatgg acctcttgga ggtccgtgaa    360
tagatttatt catgggattt gtgaattg                                        388

<210> SEQ ID NO 22
<211> LENGTH: 411
<212> TYPE: DNA
<213> ORGANISM: Homo sapiens

<400> SEQUENCE: 22
tctcctcaca gtctgacaag aggtctaagg tttggtttta attttttttcc tccagccagg     60 acccttcaca acctgattgc taagcttgtt agcatagagg tggtctaacc gctacatgag    120
ccgctcaccc ctgacaacca cactgttgta atgtatcaga aatgttgatt actacaaaat    180
```

```
acagaaacac gggcactgtg gtgccccgaa ttgggaccgg tgattcactc acatgcagag      240
atttatttca gcactaatct ccctatgtag ttttgcttta cttgctgttg ttccaagggc      300
tgttatattc tttgccctcc actccatctc actcccatct ctccccactc accctcttc       360 ccagccacct ccctcttctc caaagacttc attcaggccc ttaaggtgcc t               411
```

<210> SEQ ID NO 23
<211> LENGTH: 1050
<212> TYPE: DNA
<213> ORGANISM: Homo sapiens

<400> SEQUENCE: 23

```
cccactggct gagaacacca tggtggggag agtgacttca tttttaactc tcctccctcc      60
tcctgtatac tcaaggacgg agtctcttct tggtgccatg tgttttttag ctcctgccta     120
gtgcttctcc atgcctcttt ctaacaaaca gctgtaggcc tgggaagcag agcctctacc     180
aagtgtgaat ctctagctag aattttggcc tatggtttta acatttgcag tacatttttct    240 tctagagcac attctactta ggggaggac  accattttcc atttatgtta gtgacataaa     300 gcttcctta  aaagataaat atattttggg atggagaatt gcttgaaccc aggaggcaga     360
ggtggcagtg agccgagacc gtgccattgc actccagcct gggtgacaga gcgagactcc     420
gtcttaaaaa ataaataaaa cagggtaaaa acacagaagt tacagaagcc tggcaggaaa     480
agccaaagac agaaggctga cggaggcttt aaacgcactt cgttgacatt caggaccctc     540
gggaatattc ctcggcccta cggggtgggg ggtgtgcttg ttcttatttt ggtctcacat     600
ccttctcagg ccagccttcc tcctcctgca tggccaagca gggtgagtcc ttccttggga     660
ggccgcctgt tctctccccg cctcctggtt ctggatttgg gtagggcagg atttgggtgt     720
tcaccctcct aggaggccct gagaggctgc caggccccag ctctgcttcc tccacccact     780
gatgctgggc tcagagaagg gtggggaagg tgctgttccc ccactgatgt cacacctgct     840
cgggggcctg gttgctgctg ggggtcccct ggtatgtgct cagtggggac tctgaccgga     900
gcctggacca tggagaggag cctcagcctg tctggccctt ccctccctcc ccatggagcc     960
ttggcatgtt ccacctcctc tgccctgcac acattcacca gtgagcccca cgcaggtggg    1020 taagggttc tggagtgagt ggggggtgctg                                    1050
```

<210> SEQ ID NO 24
<211> LENGTH: 1050
<212> TYPE: DNA
<213> ORGANISM: Homo sapiens

<400> SEQUENCE: 24

```
ggcgctttga tctccacttc ccatggccaa ccccaacac  accagatacg tactcactta      60
gtggagtttg agcctgtgt  ctgtcctcct agtgtgttgg ggtcgaccag agcgattggc     120
agggaccgtc agagacagag gtttaagcag gaagagagac actttcttct gaaagtagag     180
ccactgacag cttctatttt catagaccta aatatgggct tgccacccgg ataacattac     240
acgcatggcc tctcctggtg ctccccacac ccgggtgaag tccgtgttat tattatctcc     300
atttctcagg taagagaatt gggtgagaac tagagatgtt aagcagcaag ttcccacagg     360
gctgaaggag gtgagtggta cgtcaagat  gtgaaccact gttactgcac actgaatcat     420
accactatgg ccgatcacag agggccctgg ggagccacgg aaggctctag gcagaggcag     480
ggcctcttgg gttagaagga cggcctggag ttggatcct  gccacccggc acttaccagc     540
agacacccca ccatgagatt atgtctcttg atgattgagc aaataggctc ccaggtcaaa     600
```

```
tgtcccaggt tgagtccca gcaagaaaaa agggaagagg agagagaggc agaggaaggg      660
gaaaaaaaag acagaaggaa ggagagggag aaggaggagt aggagggaag gagggaagcg      720
gggggaaaga aagatacgtg agataatatt caggtcaaat atggacagtt ttggctgggc      780
acggtggctc acgcctgtaa tcccagcact ttgggaggct gaggtgggag gatcacttaa      840
gcctgggagt tcaagaccag cctggacaac atagcaagcc gttgtctcta caaaaactat      900
aaaaactagc agggcatggt ggtgcatgcc tgtgatccca gctactgggg aggcagaggt      960
gagtggatca cttgagccca ggagttcaag atcagcctgg caacacagt gagatgaaag       1020 aaagaaagag agagagaaag agagagagag                                       1050
```

<210> SEQ ID NO 25
<211> LENGTH: 1050
<212> TYPE: DNA
<213> ORGANISM: Homo sapiens

<400> SEQUENCE: 25

```
atggccggca gccttggagg acagccccga gggctcaagg gcttggcaag cttggcaaac      60
ttgcaaatgg cagccctgga ttgcattccg cccctgcccc cactgcacag gtttgagtcc      120
cactctccca ccaggcctgt cacaaataca ctggggtcaa ccccatgttt caaggatcaa      180
gctgaccaca ccctctccct gctcagatgc tcccgcctcc cctgccttta tgccagggtg      240
ggtccgttcc ttggctgggc ttccagggca tttcaggatc tgtccctctt gcctctgagc      300
cccttgaccg ccgaccccac cgcagctctc agccctctgc ctgccacgcc ttcccctct       360 tccccagccc ccgctgagtc cagcactgcc ggcctggctc acctgcagga agcctggtag      420
ctccttctcc atcagcacct tgagctcccc cttggtcagg gtctgcgtgc tgccctcgct      480
gcccgaatat cgggaaaaga cgtctatgat catgcccatg gctgtctcta gttccgtcat      540
ggtgctagat tcagacccac cttcctcctg ggggctggca gggccgagaa aatgtcccac      600
tggcagcctc ttggtgcttt ataaggcagc ctcatattga cacagagggt gggacagtgg      660
ggttgggaca ttcaggaagt cctgcccctc cccattcatg tgctcagttc tgatgaaatg      720
catcgttgtg atgacgtttc tggaaccttt ccccagcca aggcccaggg tgtgggctgc       780
ctccaggcat ccacatttta cagtgttcac ctgtgtctcg gcgccatcac tgagccacag      840
tggcatcctc attcctggcc ctccctgggt aagtgggcac ggggtgagtg tgtgtggagt      900
gagtggtgac tccgtggccc tttgtgtcaa tatcagagcg tgctggcacc cagcgtgctg      960
acacgaggag acatctgaga gtgaattcac atgggcgtgt tgtgaacat ggatctgccc       1020 catcgtccct ttcttagagc actctgtgtc                                       1050
```

<210> SEQ ID NO 26
<211> LENGTH: 1050
<212> TYPE: DNA
<213> ORGANISM: Homo sapiens

<400> SEQUENCE: 26

```
agggaaaaaa tcatcttcat ggaaattaat tactttttta caaattgtga atttgaccct      60
taagagtttt cttcctgata tttaaaattg aaaaaaaaat tgttgacatt aatatttctt      120
ctttcctttt ttttcttttc cttttttttt tttttttgc aggtatggcc tcacaagtct       180
tggtctaccc accatatgtt tatcaaactc agtcaagtgc cttttgtagt gtgaagaaac      240
tcaaagtaga gccaagcagt tgtgtattcc aggaaagaaa ctatccacgg acctatgtga      300
```

```
atggtagaaa ctttggaaat tctcatcctc ccactaaggg tagtgctttt cagacaaaga      360
taccatttaa tagacctcga ggacacaact tttcattgca gacaagtgct gttgttttga      420
aaaacactgc aggtgctaca aaggtcatag cagctcaggc acagcaagct cacgtgcagg      480
cacctcagat tggggcgtgg cgaaacagat tgcatttcct agaaggcccc cagcgatgtg      540
gattgaagcg caagagtgag gagttggata atcatagcag cgcaatgcag attgtcgatg      600
aattgtccat acttcctgca atgttgcaaa ccaacatggg aaatccagtg acagttgtga      660
cagctaccac aggatcaaaa cagaattgta ccactggaga aggtgactat cagttagtac      720
agcatgaagt cttatgctcc atgaaaaata cttacgaagt ccttgatttt cttggtcgag      780
gcacgtttgg ccaggtagtt aaatgctgga aagagggac aaatgaaatt gtagcaatca      840
aaattttgaa gaatcatcct tcttatgccc gtcaaggtca aatagaagtg agcatattag      900
caaggctcag tactgaaaat gctgatgaat ataactttgt acgagcttat gaatgctttc      960
agcaccgtaa ccatacttgt ttagtctttg agatgctgga acaaaacttg tatgactttc     1020
tgaaacaaaa taaatttagt cccctgccac                                      1050

<210> SEQ ID NO 27
<211> LENGTH: 1050
<212> TYPE: DNA
<213> ORGANISM: Homo sapiens

<400> SEQUENCE: 27
ctgaatcttg aataggagct tgtccataga gggtcacgga tctcccacac agagagcacc       60
acaaaatcct cagcaatttg gtgagagtat ggtacaagat gatagtggcc tggggcttga      120
acaagaggct gagtgcggtg gctcacacct gtaatctcag cactttggga ggctgaggcg      180
aacacctgag gtcagcagtt cgagaccagc ctggccaaaa tggcaaaacc ccgtctctat      240
taaaaataca acattagcc gggcatggtg gcaggtgcct gtaatcccag ctactcagga      300
ggctgaggtg ggaggattgc ttgagtgtgg gaggcggagg ttgcagtgag ccagagatcat      360 gccactgcac tccagcctgg gtgacagagt gagaccctgt ctcaaaaaaa aaaaaaaaa      420 aaagttagac gtctagtaca ggaaccatgc aacacatcga gtcagccaag gcaaggtaa      480 ggagagtgat gaggaaaaag gggtggctgc cctgctcggt gctgttctgt caaagagccg      540
aaattcttcg cggggtggca gatgaggaca ggaacagctg gggtgtggca agtgttgctg      600
cctggggaga gcggagggtg aggtgtttct cacgggtgca tccagtgact catcaggaca      660
gcggagctca tgaggccatg tctcccgttt cctgccttag aatcacatga aaatgagcag      720
agggtgggtc atcaggacag ggctctccgg ggagcggaag cgccttcaat gcaggcctgt      780
gggcaggggc gtggggcgc gcacacacac acgcctgggt gacctctacg tatatacaga      840
gcctccctgg ccctcctgga aagagtcctg gaaagacaac cttcaggtcc agccctggag      900
ctggaggagt ggagcccac tctgaagacg cagcctttct ccaggttctg tctctcccat      960
tctgattctt gacaccagat gcaggtaagc agagatgaaa gggtgaggtg acggccaggg     1020
aacagcctag cctcacagat gagagtgcac                                      1050

<210> SEQ ID NO 28
<211> LENGTH: 1050
<212> TYPE: DNA
<213> ORGANISM: Homo sapiens

<400> SEQUENCE: 28
aaactggaga gatagggttt taacaagatg caaggacaat ctgaggactg agagccattt       60
```

```
caacgtgagc ccccagtctg agaacaagaa agaagaactt ctgtctcgag gtaaaaaggc      120
ctgctgggga cctggggtcc aggtgaaggg atgggatggt tgacagaact gctcaggtga      180
ggacaggctt ctcatgaggt ccctgagaaa cttgcctttt ggagggaaat gtcctctgcc      240
ctctggagcc tggggagaag gttatttctg cccgccagac cagcatgctc gcttttcttc      300
catgggcatt caggaatcct ggccccattc tgacattcct caaatggagg aattcctcaa      360
attaccagag gaaagttacc aaagtttaga tctgctggag ctcttcaagg attggcctga      420
gacaagccgg gaggtgccac ggggcttgga gctggccctg tgaggcacct ccggggaag       480 ttcatgtcct aggtggttca cgtcatggac ctcttggagg tccgtgaata gatttattca      540
tgggatttgt gaattggggg gaaaaataca tctttatttt cactaatctt taattgaaag      600
tcagcacttg cttcagttat gaatgtagac aatgaaccac aatagaattt gccatcaata      660
gaaaacacaa atattttcaa atctcattac agttttata gatttctcca aatgtcctta       720
acgctcagca ctactacaga attacaacag ttattaggct gatgtcaaat ctaaagaagc      780
atgtgtactg ctctaccaca cattcttcta atgttttgac aactgtcttg tcataatttg      840 ttcccttat tatcccatgt atcttattaa ttttaaatg ttgttctgag aagggactcc        900
atatgccttc ccagaccacc aaagaggtcc atggcgcctt tatgtcaggc acctgctttg      960
gtgtgttgag caggaagcct gagatctcag acaagagctt caagggcccc ccagcccaaa     1020
cctctgtcta ctaacaagtc tggttctact                                      1050
```

<210> SEQ ID NO 29  
<211> LENGTH: 1050  
<212> TYPE: DNA  
<213> ORGANISM: Homo sapiens

<400> SEQUENCE: 29

```
cagtacaaag tagacgcacg cacacacgct cacacacaca cagaggcagg caggcaggca       60
ggctgaacac gctggctggg aactgctgtc ggagccctct atagcaggag aggagaggga      120
gaggagagga gggagggaaa gagggaggga gggagggagc acgggagagg agggagaggg      180
agagagcagg agctccagag agggaggggag gttggtatgg aggaagggag ggaagaaggg    240
agggagggag ggagggagga gggagggagg gaggggagga gagagagaga gagagagaga    300
gagagagaga gagagagaga gagagagaga gagagagaga ggagctggat agctttaggc     360
accactgctt gttttttaaag aagcagtttg tggagaggtc atttcctgtc cacattgtag    420
actagttcac aaatataatt ctcctcacag tctgacaaga ggtctaaggt ttggttttaa     480
tttttttcct ccagccagga cccttcacaa cctgattgct aagcttgtta gcatagaggt    540
ggtctaaccg ctacatgagc cgctcacccc tgacaaccac actgttgtaa tgtatcagaa    600
atgttgatta ctacaaaata cagaaacacg ggcactgtgg tgccccgaat tgggaccggt    660
gattcactca catgcagaga tttatttcag cactaatctc cctatgtagt tttgctttac    720
ttgctgttgt tccaagggct gttatattct ttgccctcca ctccatctca ctcccatctc    780
tccccactca cccctcttcc cagccacctc cctcttctcc aaagacttca ttcaggccct    840
taaggtgcct gggcattttc aggtaaaaac agtcgttctg aatgtggaag gtataaaata    900
cacttaagga gagcaatggt cttttttccc aggaaggaaa acaaacaaa caaacaaaca     960 aaaacccaa acagacctcc caataagaca ggaaaagcaa agaaggagaa aactgccaca    1020
aaaatgacca cggaaaattt ggttgagaag                                     1050
```

US 9,840,736 B2

EPIGENETIC MARKER FOR THE IDENTIFICATION OF T LYMPHOCYTES

CROSS REFERENCE TO A RELATED APPLICATION

Figure 1:
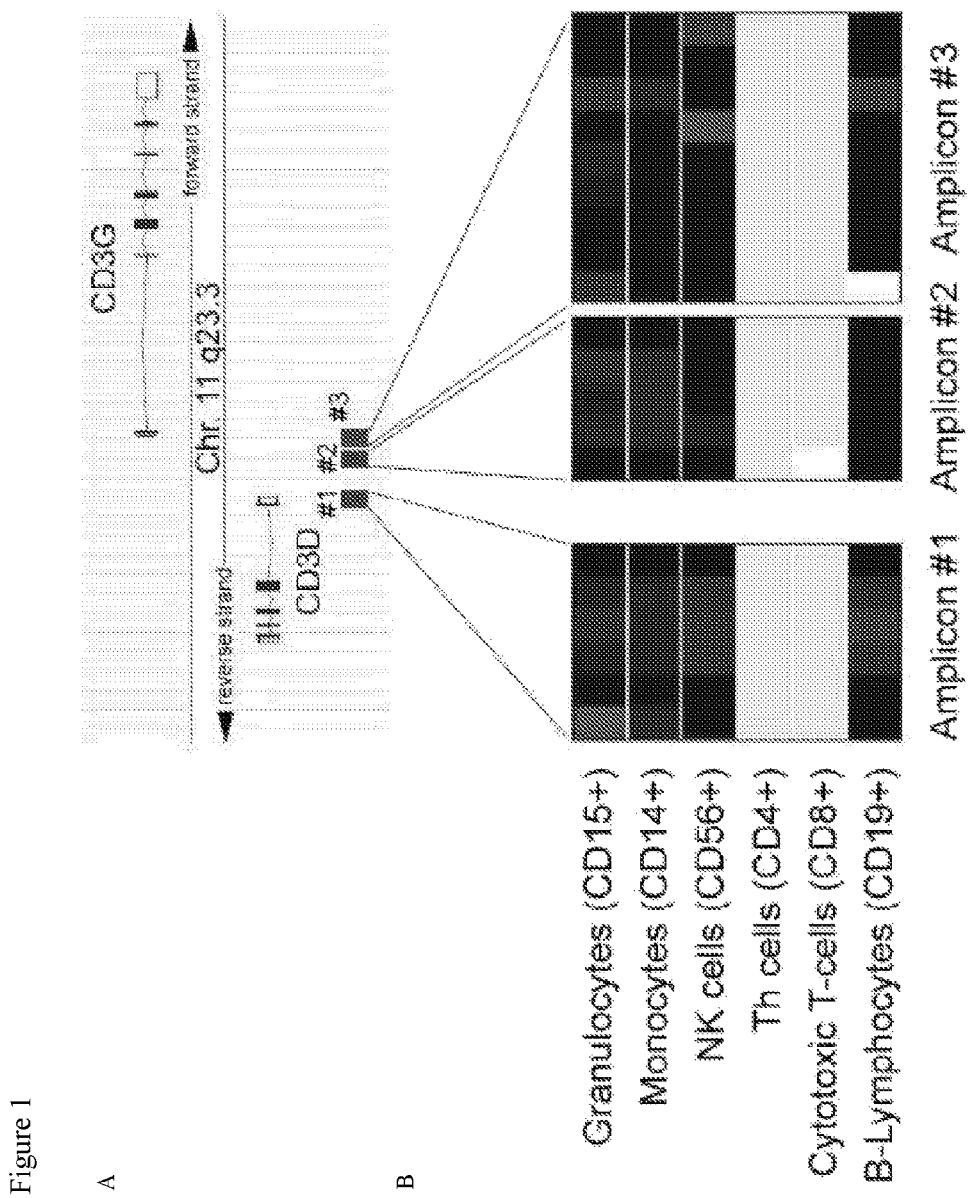
Figure 1:
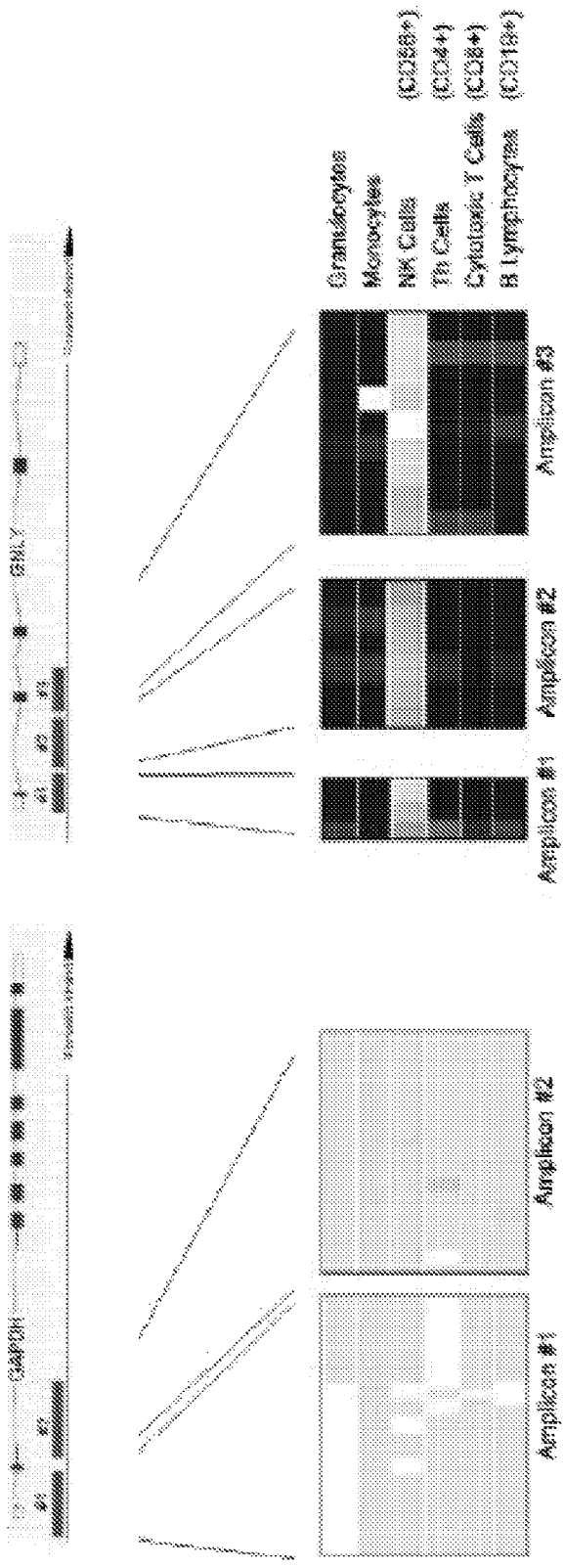

This application is a National Stage Application of International Application Number PCT/EP2011/051601, filed Feb. 3, 2011; which claims priority to European Patent Application 10001121.2, filed Feb. 3, 2010; which are both incorporated herein by reference in their entirety.

The present invention relates to a method for identifying and/or quantitating the total amount, and/or ratio of a specific type and/or state of a mammalian cell within all cells as present in a sample obtained from a mammal, comprising a) analyzing the relative amount of accessible chromatin in regions that are specific for a cell-type and/or cellular state in the genome of said cell, b) comparing said relative amount of accessible chromatin said in regions with the relative amount of accessible chromatin in regions in the genome of said cell that are unspecific for a cell-type and/or cellular state, and c) deducing the specific type and/or state of said mammalian cell in said sample based on said comparison. Preferably, said identifying further comprises a relative quantification of said specific cell type and/or state based on said comparison. The method can further comprise a diagnosis of a predisposition to a disease or a disease based on said identification. Kits and certain markers in regions of accessible chromatin in the genome are described, too.

The sequence listing as filed together with the present application is hereby incorporated in its entirety as part of the description as filed.

BACKGROUND OF THE INVENTION

Gene regulation is a complex occurrence and process in mammalian cell development and function.

In part, such complex regulation depends on proteins and the transcription machinery. The other parts depend on the accessibility of the blueprint and substrate of gene transcription, i.e., the DNA. Most gene regulation at DNA level is controlled at so-called gene promoters and similar regulatory DNA regions that serve as regulatory elements, including binding sites for transcription modulators (enhancers) and conserved non-coding regions, and the like.

One particular control instance upon/on (Greek: epi, ἐπί) the DNA in general and regulatory elements in particular is their epigenetic characterization, whereby chromatin plays an important role and describes a complex combination of DNA, RNA, and protein. Together, these combinations make up the chromatin of chromosomes. The major components of chromatin are DNA and histone proteins, although many other chromosomal proteins have prominent roles. The functions of chromatin are to package DNA into a relatively small and compact structure to strengthen the DNA to allow mitosis and meiosis, and to serve as a mechanism to control gene expression and DNA replication. Chromatin structure is also influenced and governed by chemical modifications such as methylation or hydroxymethylation (DNA and proteins) and acetylation (proteins), and non-histone modifications. The major building blocks of chromatin are the nucleosomes, and the location of the nucleosomes is determined by the chromatin structure/modification and is also epigenetically inherited.

The scientific community widely acknowledges that "open", accessible chromatin corresponds to active genes or an enablement for gene expression. Conversely, densely packed and inaccessible chromatin is widely known as deactivated, transcription locked chromatin. The respective epigenetic control is long-lasting and sustainable compared with the so-called immediate control, such as executed by transcription factors. As far as reporting of activity states is concerned, chromatin state has gained interest as a level of gene control that determines more stable gene regulation than other detectable levels.

While chromatin structure is considered a very stable process of gene regulation, it is—nevertheless—inducible. So, therefore, it can change/be changed during cellular differentiation and similar processes. However, in contrast to the transcription machinery, an induction of chromatin changes appears to remain long-lasting. Furthermore, open and closed chromatin states can have long-ranging effects in the genome, e.g. the chromatin status of an enhancer can have an effect on a not directly adjacent gene.

Even though almost all cells in an individual contain the exact same complement of DNA code, higher organisms must impose and maintain different patterns of gene expression in the various tissue types. On the one hand, some gene regulation must be transitory, depending on the current state of the cell and changes in external stimuli. Persistent regulation, on the other hand, is a primary role of epigenetics—heritable regulatory patterns that do not alter the basic genetic coding of the DNA. Chromatin structure serves as the stable memory for cells and performs a crucial role in maintaining the long-term identity of various cell types.

The immune system plays a pivotal role in the development of tumours. However, understanding the role of T-lymphocytes as major cellular component of the adaptive effector immune response and their counterpart, the T-lymphocyte subset regulatory T cells within the tumour microenvironment remains fragmentary. This is equally true for most cellular components of both innate and adaptive immunity, including natural killer cells. In part this deficiency is due to the lack of reliable technical solutions for specific cell identification and quantification in solid tissue.

Until today, quantitative characterization of immune cells including T-lymphocytes, Tregs and NK cells is mainly performed by mRNA analysis, immunohistochemistry (IHC) and/or FACS analysis. However, all three technologies are afflicted with limitations when applying them in a truly quantitative manner. RNA analysis cannot be associated to cell numbers, since it determines an overall amount of a certain transcript in a sample. Both IHC and FACS analysis depend on a threshold of proteins displayed by the cell before a cell is regarded positive for a certain marker. FACS analysis is additionally problematic for solid tissues, since an experimental prerequisite is its dissociation into a single cell suspension. Despite attempts to automate cell counting by IHC, it is not a reliable method for quantification (Taylor, C. R. and R. M. Levenson, *Quantification of immunohistochemistry—issues concerning methods, utility and semiquantitative assessment II.* Histopathology, 2006. 49(4): p. 411-24). It is widely acknowledged that those technological difficulties associated with measurements of immune cells in the tumour microenvironment constrain precise studies and the actual immunological status and the prognostic meaning of immune cell infiltration in the tumor environment remain largely unclear.

US 2009-042184 describes methods for diagnosis and monitoring the efficacy of treatment of a cancer comprising detecting an enhanced degree of chromatin modification within Chromosome 2 of the human genome from about map position 2q14.1 to about map position 2q14.3 in a sample derived from a subject. The methods also include detecting a modulated level of expression of a gene within the region of about 2q14.1 to 2q14.3 of Chromosome 2, wherein the gene may be selected from the group consisting of DEAD box polypeptide 18 (DDX18), translin (TSN), v-ral simian leukemia viral oncogene homolog B (RALB), secretin recepto (SCTR), engrailed homolog 1 (EN1), macrophage receptor with collagenous structure (MARCO), protein tyrosine phosphatase non-receptor type 4 (PTPN4), insulin induced gene 2 (INSIG2), inhibin beta B (INHBB), GLI-Kruppel family member 2 (GLI2), FLJ10996, STEAP3, diazepam binding inhibitor (DBI), MGC10993, erythrocyte membrane protein band 4.1 like 5 (EPB41L5), F1114816, or transcription factor CP2-like 1 (TFCP2L1).

US 2007-196843 (which is herewith incorporated by reference) describes methods for identifying and monitoring epigenetic modifications, such as imprinted genes, using microarray based technology. Specifically, the detection of imprinted genes by the presence of overlapping closed and open chromatin markers is described. Disclosed is a method for detecting the loss of imprinting on a genome-wide scale, which is indicative of a variety of medical conditions. Diagnostic assays and chromatin structure markers for identifying gene imprinting and loss thereof are also disclosed.

It is an object of the present invention to provide an improved method to identify and quantify cell types, in particular immune cells. Other objects of the present invention will become apparent to the person of skill upon studying the more detailed description of the present invention as follows.

According to a first aspect thereof, the present invention solves the above object by providing a method for identifying a specific type and/or state of a mammalian cell in a sample obtained from a mammal, comprising a) analyzing the relative amount of accessible chromatin in regions that are specific for a cell-type and/or cellular state in the genome of said cell, b) comparing said relative amount of accessible chromatin said in regions with the relative amount of accessible chromatin in regions in the genome of said cell that are unspecific for a cell-type and/or cellular state, and c) deducing the specific type and/or state of said mammalian cell in said sample based on said comparison.

Preferred is a method for identifying a specific type and/or state of a mammalian cell in a sample obtained from a mammal wherein said method optionally comprises b') a normalizing of the relative amount of said regions that are specific for a cell-type and/or cellular state and said regions in the genome of said cell that are unspecific for a cell-type and/or cellular state using a control plasmid as described herein.

The normalization using the accessible chromatin in a region or regions in the genome of said cell that are unspecific for a cell-type and/or cellular state (e.g. using the GAPDH-region as described herein) is the main difference and advantage of the present invention when compared with other common methods. Thus, no differential methylation is analyzed, but the "same chromatin DNA" is used. Furthermore, the standardization according to the present invention is independent from the cell-type as analyzed, which allows for an analysis of several cellular types in one sample (as also described below), depending from the choice of cell-types to be analyzed. This approach is not possible in other systems, as these are analyzing only one type of gene (e.g. foxp3 tpg is detected and compared with foxp3 cpg). In contrast, the present invention measures (for example) cd3, foxp3, gnly, 1588nk 1586grc, and/or ccr6 tpg against the "internal standard" Gapdh tpg in order to obtain a relative amount. Furthermore, in a preferred embodiment, the method also allows to measure the number of copies of the genes as analyzed can be measured using a control plasmid containing the regions to be analyzed as described herein.

The DNA blueprint must provide information for each and every function that a cell can possibly fulfill. Therefore, the information for a brain cell is also mandatory present in a liver cell. However, neither during development nor in adulthood there is need for a liver cell to express brain specific genes. Therefore, brain specific genes are permanently switched off in the liver.

As the prime determinator of this long term regulation, epigenetic changes and chromatin fully enable or prohibit stable gene expression by adopting either of the following two chromatin states:

A) Full and permanent inactivation (even of a whole chromosome), as observed with the Barr bodies of the x-chromosome. X-chromosomal inactivation is, however, a prominent exception to the general rule for genes that are switched off, since it switches off only one allele, such as, for example, in the case of the genes foxp3 and CD3.

B) Full and permanent activation of genes are exemplified by housekeeping genes. These genes are permanently required for survival of a cell, such as, but not limited to, glucose metabolism, citric acid cycle, or the urea cycle, the HMG-CoA-reductase-pathway and others. Any living cell can usually not afford to switch those cycles off, unless it (the cell) is dying or goes into lethal resting.

For further differentiation of cells in the body, there are genes that are switched on only in certain cells at certain parts of the body (organs, tissues) and/or at defined time points and periods. These cells differentiate, and by doing so, they allow the expression of certain genes, while rendering others into the large group into fully disabled genes. Principally, these (more) cell type specific genes also segregate into two groups:

i) Genes that are important switches/play an important role during embryonic development and are not required in adulthood, including genes like Oct-3 or Nanog and others, and ii) Genes with an important role during terminal differentiation to a very specific cell type and/or with an expression pattern characteristic for this cell type that are switched off during development and only enabled for expression upon terminal differentiation to a very specific cell type.

In view of the above, the present invention is based on the finding that every different distinctive cell type contains certain DNA fragments (i.e. chromosomal regions and/or genes) that have accessible chromatin region specific only to this cell type, certain DNA sections that have accessible chromatin they share with one or more groups of cells, and certain DNA fragments that have accessible chromatin that they share with all other living cells in the body. Therein, accessible chromatin in living cells can be defined by one or more of the following properties: i) DNA that contains cytosines which are accessible to conversion by bisulfite (this property is preferred, since the accessibility of DNA to the modification by bisulfite is a stable property that is retained even after purification of DNA and can thus be employed any time to analytical systems that use isolated cellular DNA);

ii) accessibility to DNAse I or similar enzymes (of note, this accessibility can be measured only as long as chromatin structure is still maintained, and thus isolation of DNA destroys this property); and iii) precipitation by ChIP; or other suitable methods known in the art.

Preferred is a method according to the present invention, wherein said identifying further comprises a relative quantification of said specific cell type and/or state based on said comparison. Further preferred is the method according to the present invention, further comprising a step of determining a specific cell-type and/or cellular state comprising measuring the relative amount of accessible chromatin in the genome of a cell having a known specific cell-type and/or cellular state prior to step a).

The present invention establishes an analytical method and system that identifies and quantifies in one preferred embodiment all possible cells, i.e., all cell types, and in a second embodiment preferably all immune cells, and in a third embodiment the specific immune cells as described herein, by measuring the relative amount of accessible, i.e., active chromatin in cell type and cell status specific regions versus accessible chromatin being accessible in all cell types.

Further preferred is a method according to the present invention, further comprising generating a knowledge base comprising information on the relative amount of accessible chromatin in the genome of cells having a known specific cell-type and/or cellular state. Said knowledge base can be a diagnostic computer, and can be fully or largely automated, such as a robot. Furthermore, the database can be centralized in order to collect information about accessible chromatin in certain cell types or cellular states.

In a further preferred embodiment of the method according to the invention, the analysis comprises measuring the relative amount of accessible chromatin with an assay comprising DNAse I digestion, ChIP chromatin immunoprecipitation microarray (e.g., ChIP), quantitative PCR analysis, selective precipitation or conversion of cytosines with bisulfite, or combinations thereof. In yet another preferred embodiment of the present invention, in order to diagnostically determine the location of nucleosomes, a DNAse I hypersensitivity assay is used as described herein.

Other examples for methods which can be used in the context of the present invention in order to identify areas of open chromatin are as follows. In certain embodiments, a molecule which is capable of binding to an accessible region, but does not necessarily cleave or covalently modify DNA in the accessible region, can be used to identify and isolate accessible regions.

Suitable molecules include, for example, minor groove binders (e.g., U.S. Pat. Nos. 5,998,140 and 6,090,947), and triplex-forming oligonucleotides (TFOs, U.S. Pat. Nos. 5,176,996 and 5,422,251). The molecule is contacted with cellular chromatin, the chromatin is optionally deproteinized, then fragmented, and fragments comprising the bound molecule are isolated, for example, by affinity techniques. Use of a TFO comprising poly-inosine (poly-I) will lead to minimal sequence specificity of triplex formation, thereby maximizing the probability of interaction with the greatest possible number of accessible sequences.

In a variation of the aforementioned methods, TFOs with covalently-attached modifying groups are used. See, for example, U.S. Pat. No. 5,935,830. In this case, covalent modification of DNA occurs in the vicinity of the triplex-forming sequence. After optional deproteinization and fragmentation of treated chromatin, marked fragments are purified by, for example, affinity selection.

In another embodiment, cellular chromatin is contacted with a non-sequence-specific DNA-binding protein. The protein is optionally cross-linked to the chromatin. The chromatin is then fragmented, and the mixture of fragments is subjected to immuno-precipitation using an antibody directed against the non-sequence-specific DNA-binding protein. Fragments in the immuno-precipitate are enriched for accessible regions of cellular chromatin. Suitable non-sequence-specific DNA-binding proteins for use in this method include, but are not limited to, prokaryotic histone-like proteins such as the bacteriophage SP01 protein TF1 and prokaryotic HU/DBPII proteins. Greene et al. (1984) Proc. Natl. Acad. Sci. USA 81:7031-7035; Rouviere-Yaniv et al. (1977) Cold Spring Harbor Symp. Quant. Biol. 42:439-447; Kimura et al. (1983) J. Biol. Chem. 258:4007-4011; Tanaka et al. (1984) Nature 310:376-381. Additional non-sequence-specific DNA-binding proteins include, but are not limited to, proteins containing poly-arginine motifs and sequence-specific DNA-binding proteins that have been mutated so as to retain DNA-binding ability but lose their sequence specificity. An example of such a protein (in this case, a mutated restriction enzyme) is provided by Rice et al. (2000) Nucleic Acids Res. 28:3143-3150.

In yet another embodiment, a plurality of sequence-specific DNA binding proteins is used to identify accessible regions of cellular chromatin. For example, a mixture of sequence-specific DNA binding proteins of differing binding specificities is contacted with cellular chromatin, chromatin is fragmented and the mixture of fragments is immuno-precipitated using an antibody that recognizes a common epitope on the DNA binding proteins. The resulting immuno-precipitate is enriched in accessible sites corresponding to the collection of DNA binding sites recognized by the mixture of proteins. Depending on the completeness of sequences recognized by the mixture of proteins, the accessible immuno-precipitated sequences will be a subset or a complete representation of accessible sites.

In addition, synthetic DNA-binding proteins can be designed in which non-sequence-specific DNA-binding interactions (such as, for example, phosphate contacts) are maximized, while sequence-specific interactions (such as, for example, base contacts) are minimized. Certain zinc finger DNA-binding domains obtained by bacterial two-hybrid selection have a low degree of sequence specificity and can be useful in the aforementioned methods. Joung et al. (2000) Proc. Natl. Acad. Sci. USA 97:7382-7387; see esp. the "Group III" fingers described therein.

As further examples, in selective/limited digestion methods (as also mentioned above), the limited nuclease digestion approach generally involves treating nuclei or chromatin under controlled reaction conditions with a chemical and/or enzymatic probe such that small fragments of DNA are generated from accessible regions. The selective and limited digestion required can be achieved by controlling certain digestion parameters. Specifically, one typically limits the concentration of the probe to very low levels. The duration of the reaction and/or the temperature at which the reaction is conducted can also be regulated to control the extent of digestion to desired levels. More specifically, relatively short reaction times, low temperatures and low concentrations of probe can be utilized. Any of a variety of nucleases can be used to conduct the limited digestion. Both non-sequence-specific endonucleases such as, for example, DNase I, S1 nuclease, and mung bean nuclease, and sequence-specific nucleases such as, for example, restriction enzymes, can be used.

A variety of different chemical probes can be utilized to cleave DNA in accessible regions. Specific examples of suitable chemical probes include, but are not limited to, hydroxyl radicals and methidiumpropyl-EDTA Fe(II) (MPE). Chemical cleavage in accessible regions can also be accomplished by treatment of cellular chromatin with reagents such as dimethyl sulfate, hydrazine, potassium permanganate, and osmium tetroxide, followed by exposure to alkaline conditions (e.g., 1 M piperidine). See, for example, Tullius et al. (1987) Meth. Enzymology, Vol. 155, (J. Ableson and M. Simon, eds.) Academic Press, San Diego, pp. 537-558; Cartwright et al. (1983) Proc. Natl. Acad. Sci. USA 80:3213-3217; Hertzberg et al. (1984) Biochemistry 23:3934-3945; Wellinger et al. in Methods in Molecular Biology, Vol. 119 (P. Becker, ed.) Humana Press, Totowa, N.J., pp. 161-173; and Maxam et al. (1980) Meth. Enzymology, Vol. 65, (L. Grossman and K. Moldave, eds.) Academic Press, New York, pp. 499-560. When using chemical probes, reaction conditions are adjusted so as to favor the generation of, on average, two sites of reaction per accessible region, thereby releasing relatively short DNA fragments from the accessible regions.

As with the previously-described methods, the resulting small fragments generated by the digestion process can be purified by size (e.g., gel electrophoresis, sedimentation, gel filtration), preferential solubility, or by procedures which result in the separation of naked nucleic acid (i.e., nucleic acids lacking histones) from bulk chromatin, thereby allowing the small fragments to be isolated and/or cloned, and/or subsequently analyzed by, for example, nucleotide sequencing.

In one embodiment of this method, nuclei are treated with low concentrations of DNase I; DNA is then purified from the nuclei and subjected to gel electrophoresis. The gel is blotted and the blot is probed with a short, labeled fragment corresponding to a known mapped DNase I hypersensitive site located, for example, in the promoter of a housekeeping gene. Examples of such genes (and associated hypersensitive sites) include, but are not limited to, those in the genes encoding rDNA, glyceraldehyde-3-phosphate dehydrogenase (GAPDH) and core histones (e.g., H2A, H2B, H3, H4). Alternatively, a DNA fragment size fraction is isolated from the gel, slot-blotted and probed with a hypersensitive site probe and a probe located several kilobases (kb) away from the hypersensitive site. Preferential hybridization of the hypersensitive site probe to the size fraction is indicative that the fraction is enriched in accessible region sequences. A size fraction enriched in accessible region sequences can be cloned, using standard procedures, to generate a library of accessible region sequences.

As used herein, the term "accessible chromatin" refers to a region of chromatin in which the DNA base cytosine is generally—and independent of the nucleotide context—accessible to conversion by bisulfite to uracil. Such regions are preferably also defined by the fact that the unpurified DNA is at least 10-fold more sensitive to the action of an endonuclease, e.g., DNAse I, than surrounding regions. Because opening of the chromatin is a prerequisite to transcription activity, DNAse I sensitivity provides a measure of the transcriptional potentiation of a chromatin region; greater DNAse sensitivity generally corresponds to greater transcription activity. DNAse hypersensitivity assays are described by Weintraub and Groudine, 1976, Science 193: 848-856, incorporated herein by reference. "Highly transcribed" or "highly expressed" regions or genes are regions of open chromatin structure that are transcribed. Recently researchers have found that regions that are rich in genes tend to be in open chromatin structures, whereas regions poor in genes tend to be in compact chromatin. However, open chromatin can contain inactive genes and compact chromatin can contain active genes. (See Bickmore, et al (2004) Chromatin Architecture of the Human Genome: Gene-Rich Domains Are Enriched in Open Chromatin Fibers, Cell, Vol 118, 555-566, 3.)

Non-completely bisulfite-converted DNA is DNA that retains cytosine residues in its sequence after the treatment with bisulfite instead of converting it to uracil at these positions. Due to the chemical properties of the DNA it is acknowledged in the state of the art that this incomplete conversion is only occurring in the context of CpG dinucleotides and is due to restricted availability of this base caused by epigenetic modifications, such as methylation, hydroxymethylation or other covalent modifications of the cytosine base or structural changes.

Sodium bisulfite treatment or treatment with similar salts of genomic DNA was performed according to Olek et al. (Olek, A., Oswald, J., Walter, J. (1996) Nucleic Acids Res. 24, 5064-5066) with minor modifications, resulting in the conversion of chemically unmodified or "accessible" cytosine to uracil, whereas cytosines covalently modified are inert or "inaccessible" to bisulfite salts and remain unchanged when forwarded to this reaction. So therefore, only for unmodified and "accessible" cytosines in the DNA—a term that is congruently used here to accessible chromatin regions—the uracil that is generated by bisulfite or similar reactions is replaced by thymine in a subsequent PCR amplification due to the typical base pairing of DNA and RNA. Thus, detection of a "C" in sequencing reactions reflects the "inaccessibility" of chromatin and thus the modification of the genomic DNA in that DNA section. Hence it reflects closed an inaccessible chromatin. In contrast, detection of a "T" at the same site instead, reflects the absence of stable modifications and corresponds to accessible chromatin at that site and the genomic cytosine. Most references attribute this inaccessibility to methyl modifications of the 5'C position in the cytosine, although surprising new research has shown that cytosine "methylation" is clearly not the only cytosine modification (see e.g. *BMC Genomics* 2006, 7:98) that protects DNA integrity and renders chromatin inaccessible. It is, however, clear that the absence of Cytosine residues in bisulfite converted DNA is a definitive hint for a fully accessible, functionally fully active and not-chemically modified cytosine residue, regardless of what may have been the original modification at that site.

The dinucleotide CpG is severely underrepresented in mammalian genomes relative to its expected statistical occurrence frequency of 6.25%. In addition, the bulk of CpG residues in the genome are methylated (with the modification occurring at the 5-position of the cytosine base). As a consequence of these two phenomena, total human genomic DNA is remarkably resistant to, for example, the restriction endonuclease Hpa II, whose recognition sequence is CCGG, and whose activity is blocked by methylation of the second cytosine in the target site.

An important exception to the overall paucity of demethylated Hpa II sites in the genome are exceptionally CpG-rich sequences (so-called "CpG islands") that occur in the vicinity of transcriptional start sites, and which are accessible to the transcription machinery (i.e., open chromatin and no cytosine modification) in the promoters of active genes. (Jones et al. (1999) Nature Genet. 21:163-167. Aberrant hypermethylation of such promoter-associated CpG islands is a well-established characteristic of the genome of malignant cells. Robertson et al (2000) Carcinogenesis 21:61-467.

Accordingly, another option for generating accessible regions relies on the observation that, whereas most CpG dinucleotides in the eukaryotic genome are methylated at the C5 position of the C residue, CpG dinucleotides within the CpG islands of active genes are unmethylated. See, for example, Bird (1992) Cell 70:5-8; and Robertson et al. (2000) Carcinogenesis 21:461-467. Indeed, methylation of CpG is one mechanism by which eukaryotic gene expression is repressed. Accordingly, digestion of cellular DNA with a methylation-sensitive restriction enzyme (i.e., one that does not cleave methylated DNA), especially one with the dinucleotide CpG in its recognition sequence, such as, for example, Hpa II, generates small fragments from unmethylated CpG island DNA. For example, upon the complete digestion of genomic DNA with Hpa II, the overwhelming majority of DNA will remain >3 kb in size, whereas the only DNA fragments of approximately 100-200 bp will be derived from demethylated, CpG-rich sequences, i.e., the CpG islands of active genes. Such small fragments are enriched in regulatory regions that are active in the cell from which the DNA was derived. They can be purified by differential solubility or size selection, for example, cloned to generate a library, and their nucleotide sequences determined and placed in one or more databases. Arrays comprising such sequences can be constructed.

Digestion with methylation-sensitive enzymes, optionally in the presence of one or more additional nucleases, can be conducted in whole cells, in isolated nuclei, with bulk chromatin or with naked DNA obtained after stripping proteins from chromatin. In all instances, relatively small fragments are excised and these can be separated from the bulk chromatin or the longer DNA fragments corresponding to regions containing methylated CpG dinucleotides. The small fragments including non-methylated CpG islands can be isolated from the larger fragments using various size-based purification techniques (e.g., gel electrophoresis, sedimentation and size-exclusion columns) or differential solubility (e.g., polyethyleneimine, spermine, spermidine), for example. As indicated above, a variety of methylation-sensitive restriction enzymes are commercially available, including, but not limited to, Dpn II, Mbo I, Hpa II and Cla I. Each of the foregoing is available from commercial suppliers such as, for example, New England BioLabs, Inc., Beverly, Mass.

In another embodiment, enrichment of regulatory sequences is accomplished by digestion of deproteinized genomic DNA with agents that selectively cleave AT-rich DNA. Examples of such agents include, but are not limited to, restriction enzymes having recognition sequences consisting solely of A and T residues, and single strand-specific nucleases, such as S1 and mung bean nuclease, used at elevated temperatures. Examples of suitable restriction enzymes include, but are not limited to, Mse I, Tsp509 I, Ase I, Dra I, Pac I, Psi I, Ssp I and Swa I. Such enzymes are available commercially, for example, from New England Biolabs, Beverly, Mass. Because of the concentration of GC-rich sequences within CpG islands (see, above), large fragments resulting from such digestion generally comprise CpG island regulatory sequences, especially when a restriction enzyme with a four-nucleotide recognition sequence consisting entirely of A and T residues (e.g., Mse I, Tsp509 I), is used as a digestion agent. Such large fragments can be separated, based on their size, from the smaller fragments generated from cleavage at regions rich in AT sequences. In certain cases, digestion with multiple enzymes recognizing AT-rich sequences provides greater enrichment for regulatory sequences.

Alternatively, or in addition to a size selection, large, CpG island-containing fragments generated by these methods can be subjected to an affinity selection to separate methylated from unmethylated large fragments. Separation can be achieved, for example, by selective binding to a protein containing a methylated DNA binding domain (Hendrich et al. (1998) Mol. Cell. Biol. 18:6538-6547; Bird et al. (1999) Cell 99:451-454) and/or to antibodies to methylated cytosine. Unmethylated large fragments are likely to comprise regulatory sequences involved in gene activation in the cell from which the DNA was derived. As with other embodiments, polynucleotides obtained by the aforementioned methods can be cloned to generate a library of regulatory sequences and/or the regulatory sequences can be immobilized on an array.

Regardless of the particular strategy employed to purify the unmethylated CpG islands from other fragments, the isolated fragments can be cloned to generate a library of regulatory sequences. The nucleotide sequences of the members of the library can be determined, optionally placed in one or more databases, and compared to a genome database to map these regulatory regions on the genome.

In yet a further preferred embodiment of the method according to the invention, the said conversion of cytosines further comprises the analysis of chemically unmodified DNA, in particular loss of gene imprinting in at least one region of the chromosome. In order to determine chemically unmodified CpG positions, any known method to identify and discriminate unmodified DNA can be used, as described herein and in the respective literature. In a preferred embodiment of the method according to the present invention, the analysis of the accessibility status comprises a method selected from methylation specific enzymatic digests, bisulphite sequencing, analysis selected from promoter modification analysis, CpG island analysis, MSP, HeavyMethyl, MethyLight, Ms-SNuPE or any other method relying on a detection of amplified DNA. These methods are well known to the person of skill, and can be found in the respective literature.

The term "region" in the context of methylation analysis refers to a part of the chromosome containing CpG positions, in particular in parts that are relevant for the regulation of the expression of genes, such as in promoters and other regulatory elements. In particular, promoter regions as well as exon intron borders can be considered as respective regions. These regions at the same time are a preferred subgroup of regions to analyze the chromatin structure. In a further preferred embodiment of the method according to the invention, the regions that are analyzed that are specific for a cell-type and/or cellular state in the genome of said cell are selected from regions comprising a gene selected from FOXP3, GNLY, CD3, platelet glycoprotein IX (GP9); low affinity immunoglobulin epsilon Fc-receptor (FCER2); protein S100-P (S100 calcium-binding protein P); homeodomain-interacting protein kinase 3 (HIPK3); transmembrane 4 L6 family member 19 (TM4SF19); CD160 antigen precursor (Natural killer cell receptor BY55) (CD160); LIM domain-binding protein 2 (LDB2); CD19; CD3; CD8; CD15; CD14; CD56; and CD4. In a further preferred embodiment of the method according to the invention, the regions that are analyzed that are specific for a cell-type and/or cellular state in the genome of said cell are selected from the amplicons for the genes as analyzed as described herein (SEQ ID Nos. 16 to 22), as well as the respective ROIs (regions of interest, SEQ ID Nos. 23 to 29) which include the amplicon sequences.

As other examples, lung-specific gene products include the lung surfactant proteins SP-A, SP-B, SP-C, SP-D, and Clara cell secretory protein (CCSP). Other genes for certain cell-types are know to the person of skill, and can be identified using, e.g., gene expression profiling, preferably using chip assay technology, or are listed in respective databases, such as the LSPD (Liver Specific Gene Promoter Database, http://rulai.cshl.org/LSPD/index.html) or described in the literature, such as in Abbas et al. (Abbas A R, Baldwin D, Ma Y, Ouyang W, Gurney A, Martin F, Fong S, van Lookeren Campagne M, Godowski P, Williams P M, Chan A C, Clark H F. Immune response in silico (IRIS): immune-specific genes identified from a compendium of microarray expression data. Genes Immun. 2005 June; 6(4): 319-31.). The data can be preferably entered into a knowledge base, as described above.

Whereas previous analyses focused on the measurement of the methylation status, i.e., the difference of copy numbers found for methylated to unmethylated DNA in a particular DNA region, the most preferred embodiment of the present invention is independent from any modification occurring in genomic DNA. By determining fully accessible chromatin and DNA, methylation or any other modification becomes irrelevant, since only those DNA copies are accessed that are fully unmodified. Of these fully unmodified DNA, the present invention analyzes cell type specifically accessible genes and/or regions and compares them to genes and/or regions that are accessible in a larger (preferably) arbitrarily selected subgroup of cells, which may consist of two, three or all cell types in an organism (e.g., accessible FOXP3 compared with accessible CD3, compared with accessible GAPDH). Based on such system, the relative quantification of cell numbers of different cell subtypes is possible. Such direct multiplexable inter-subtype comparison is only possible with the system according to the present invention, and is not possible when differential methylation or other techniques are used.

As stated above, the present invention uses the accessibility of DNA as a prerequisite for the activity of genes. The present invention demonstrates this using GAPDH as a housekeeping gene (HKG) and a model for the general and permanent accessibility of the DNA in the promoter of HKGs. This permanent accessibility of the DNA in the promoter does not exist in cell type specific genes. Thus, a measurement, determination and analysis of the ratio of the number of specific open (accessible) genes to the number of open HKGs serves as a quantifier for the relative cell number of specific cells or specific cellular statuses. Preferably, fully bisulfite converted DNA can be used for this purpose, by comparing the amount of fully bisulfite converted DNA in a cell specific gene locus with a cell unspecific (or a pre-selected subgroup of these genes, such as, for example, the CD3 subgroup or the like) gene locus, thus reflecting the specific cells or specific cellular states, and—in addition—preferably also cell counts and quality.

A housekeeping gene (HKG) is typically a constitutively expressed gene that is transcribed at a relatively constant level and in all living cells. The housekeeping gene's products are typically needed for maintenance of the (any) cell. Expression of housekeeping genes are used as internal standards in (reverse transcription) quantitative polymerase chain reactions since it is generally assumed that their expression is unaffected by experimental conditions. Some common housekeeping genes utilized include: Actin, GAPDH, aldolase, hexokinase, cyclophilin. Housekeeping genes possess CpG-rich islands at the promoter region that are defined by their chromatin accessibility (and transcriptional activity) in all cell types, whereas cell-specific genes are shut down and their chromatin is inaccessible to the transcription machinery in all tissues except the tissue where the gene product is required and, hence, the gene is expressed. These chromatin accessibility patterns obviously correlate with gene expression. Therefore, in a further preferred embodiment of the method according to the invention, said regions that are unspecific for a cell-type and/or cellular state are selected from regions comprising a housekeeping gene, such as GAPDH.

In a preferred example, both types of genes (i.e., those with a cell type specifically accessible/inaccessible chromatin and one or more of a generally accessible chromatin structure) in their accessible version are forwarded to conversion by bisulfite, amplified and cloned into a plasmid. Further preferred is a plasmid that contains constructs of all genes in their fully accessible states in question in the form equivalent to its fully bisulfite converted amplificate, a recombinant control plasmid is described in the examples and Figures below. In a preferred aspect, quantification for a real time PCR assay is achieved by providing such standardizing plasmid, which is quantified by absorption measurement in nanodrop or alternative methods such as UVette analysis or Q-bit system (Invitrogen), by determination of its amount by the optical density. Based on this measurement, a concentration of the plasmid is determined and a standard measurement row is made by the application of a serial dilution of the measured plasmid. By this means (i.e., when a single plasmid contains all tested genes), a standard is prepared and determined (provided) that is exactly equimolar for all genes on the plasmid. While this absolute equimolarity is a preferred embodiment, and the present inventors propose to use this standardization system for all samples, an analysis is also envisaged with a similar system, if various different standards are employed, which might be on different plasmids or even do not consist of plasmid or DNA standards. Most preferred, said system comprises suitable regions to be amplified of CD3, FOXP3, GLNY, CCR6, CAMTA1, GP9, FCER2, S-100-P, HIPK-3, TM4SF19; CD160 antigen precursor, LDB2, CD19, and GAPDH.

She et al (in: She X, Rohl C A, Castle J C, Kulkarni A V, Johnson J M, Chen R. Definition, conservation and epigenetics of housekeeping and tissue-enriched genes. BMC Genomics. 2009 Jun. 17; 10:269) describe housekeeping genes (HKG) as constitutively expressed in all tissues while tissue-enriched genes (TEG) are expressed at a much higher level in a single tissue type than in others. HKGs serve as valuable experimental controls in gene and protein expression experiments, while TEGs tend to represent distinct physiological processes and are frequently candidates for biomarkers or drug targets. The genomic features of these two groups of genes expressed in opposing patterns may shed light on the mechanisms by which cells maintain basic and tissue-specific functions. Gene expression profiles of 42 normal human tissues on custom high-density microarrays were generated to systematically identify 1,522 HKGs and 975 TEGs and compile a small subset of 20 housekeeping genes which are highly expressed in all tissues with lower variance than many commonly used HKGs.

In another aspect of the method according to the present invention, the biological sample is selected from the group consisting of blood or fractions thereof, saliva, buccal, tears, semen, urine, sweat, fecal material, skin and hair. Alternatively, fixed samples on, for example, histological slides, can also be used.

In yet another preferred aspect of the method according to the present invention, the cell type is selected from an immune cell, such as a CD19+ B cell, CD3+ CD8+ cytotoxic T cell, CD15+ granulocyte, CD14+ monocyte, CD56+ natural killer cell, CD4+ helper T cell; kidney cell; bone cell;

neuronal cell; blood cell; lung cell; colon cell; and a precursor of any of these, excluding human embryonic stem cells.

In the context of the present invention, a "cell status" shall mean the biological activity of the cell in its life cycle, such as cell division, apoptosis, resting stage, chromosomal replication, production of enzymes and/or secretion of factors, and the like.

In yet another preferred aspect of the method according to the present invention, the method further comprises a diagnosis of a predisposition to a disease or a disease based on said identification. This may be achieved by determining the amount of cells with a specific cell identifier compared with the amount of all cells.

Treating a disease includes inhibiting or preventing the partial or full development or progression of a disease (e.g., ovarian cancer and/or breast cancer), for example in a person who is known to have a predisposition to a disease. An example of a person with a known predisposition is someone having a history of cancer in his or her family, or who has been exposed to factors that predispose the subject to a condition, such as exposure to radiation. Furthermore, treating a disease refers to a therapeutic intervention that ameliorates at least one sign or symptom of a disease or pathological condition, or interferes with a pathophysiological process, after the disease or pathological condition has begun to develop. By way of example, in cancer a treatment can be selected from chemotherapy, radiotherapy, or surgical removal of the affected tissue and/or surrounding area, and combinations of the given treatment options. Another aspect of the present invention relates to a method for diagnosing or prognosing development or progression of a disease, such as cancer in a subject, comprising a method according to present invention, and diagnosing or prognosing development or progression of said disease cancer based on said determinations. This in a preferred embodiment include the determination of the immune status of an individual, for which the present inventors assume that this method provides the best known means. The knowledge of the immune status may also aid in predicting the treatment as well as the general prognosis of a patient.

The results of the comparisons as above can also be used to diagnose or provide a prognosis of progression of a disease, such as cancer, in a subject. The patterns of expression can also be used to screen for therapeutic agents for the treatment of a disease, such as cancer, or monitoring response to therapy in a subject, by looking for a return of the patterns of expression of the a disease, such as cancer, toward a non-tumor tissue pattern.

Preferred is a method according to the present invention, wherein the disease is selected from the group consisting of immune diseases or conditions, cancer, birth defects, mental retardation, obesity, neurological disease, diabetes, and gestational diabetes. Preferably, said cancer is selected from the group consisting of colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, and adenomas.

Yet another aspect of the invention relates to a method for monitoring the effect of a drug on the relative amount of a specific type and/or the state of a mammalian cell in a sample obtained from a mammal, comprising performing the method according to the present invention in a mammal treated with said drug, and comparing the relative amount of said specific type and/or the state of said mammalian cell with an untreated sample. The presence and change of numbers, quantities or ratios of cells with an open chromatin at particular marker genes as discussed herein (either increase or decrease) is indicative for a response and/or likelihood of a response of said patient to said treatment. No changes of the cell specifically accessible gene copies usually indicate no effect of the therapy as chosen. Monitoring or predicting can also be combined with other methods, such as, for example, CA125 blood tests and/or CT scans or ultrasound scans that are known in the art Preferred is a method according to the present invention, wherein the biological sample is selected from the group consisting of blood or fractions thereof, saliva, buccal, tears, semen, urine, sweat, faecal material, skin and hair as also mentioned above. Furthermore, the sample can comprise any type of cells from healthy or diseased solid tissue, such as but not limited to, heart, liver, brain, kidney, bladder, muscle, cartilage, bone, colon, stomach, breast, pancreas, and/or thyroid. Preferably, the cell type is selected from an immune cell, such as a CD19+ B cell, CD3+ CD8+ cytotoxic T cell, CD15+ granulocyte, CD14+ monocyte, CD56+ natural killer cell, CD4+ helper T cell; kidney cell; bone cell; neuronal cell; blood cell; and a precursor of any of these, excluding totipotent human embryonic stem cells.

Again, preferred is a method according to the present invention, wherein the disease is selected from the group consisting of immune diseases or conditions, cancer, birth defects, mental retardation, obesity, neurological disease, diabetes, and gestational diabetes. Preferably, said cancer is selected from the group consisting of colorectal cancer, esophageal cancer, stomach cancer, leukemia/lymphoma, lung cancer, prostate cancer, uterine cancer, breast cancer, skin cancer, endocrine cancer, urinary cancer, pancreatic cancer, other gastrointestinal cancer, ovarian cancer, cervical cancer, head cancer, neck cancer, and adenomas.

Still another aspect then relates to a method for determining the presence of a cell in a biological sample, comprising the step of determining the chromatin structure of at least one of the genes selected from the group of GP9, FCER2, S100P, HIPK3, TM4SF19, CD160, and LDB2, whereby a profile (or panel) is generated that is specific for the cellular characteristics of a selected cell.

Thus, in another aspect thereof, the present invention refers to specific marker genes as mentioned above whose chromatin structure as determined using, for example, real time PCR analysis of completely bisulfite converted, totally cytosine free DNA, was surprisingly found to be indicative for certain cell types and statuses. In one aspect of the present invention, these genes can therefore be used as preferred examples to characterize cell types and statuses in biological samples that contain a mixture of, for example, cells of unknown type and/or status.

Preferred is a method according to the present invention, wherein the chromatin structure of at least two of said genes, preferably one cell type specific and one generally accessible, is determined. Preferred is further a method according to the present invention, wherein the chromatin structure of all of said genes is determined. The genes that form the basis of the present invention are preferably to be used to form a "gene panel", i.e. a collection comprising their respective informative chromatin structure, for a particular cell type or a group (set) of cell types, respectively. The formation of gene panels allows for a quick and specific analysis which is indicative for particular cell types and statuses. The gene panel(s) as described and employed in this invention can furthermore be used with surprisingly high efficiency for the determination of the presence of a cell in a biological sample. In addition, the use of multiple CpG sites from a diverse array of genes allows for a high degree of sensitivity and specificity in comparison to single gene diagnostic and detection tools.

In another aspect thereof, the method according to the present invention further comprises a specific selection of the genes to be determined based on the quality of the chromatin structure analysis for a selected cell type. This is, while the broad panel with the fourteen genes may be employed for distinguishing a group of cell types with a high resolution for distinguishing and quantifying accuracy, it is possible to use only a fraction of the panel for the identification and quantification of a smaller group of cell types. In cases where it is known that not all cell types may be present or relevant for the analysis, a selected panel consisting of less markers than all fourteen may be used. For example, in a case where a differentiation experiment is performed with stem cells that produce only a subset of cell types within the respective differentiation pathway, there is demand only for the analysis of some cell types and their differential chromatin structure patterns. In this case, a mini-marker panel may be generated for this purpose, with less than the full set of fourteen marker regions to achieve both identification and quantification of the investigated population. In the most extreme case, such mini panel may—in dependence on the addressed question—consist of no more than one marker region. This minimal scenario is feasible in two situations. On one hand such situation could occur when only two cell types are possibly present in a heterogeneous cell population. In this case, a single marker region that has a consistent and distinctive chromatin structure between the two cell types is capable of distinguishing them. Alternatively, such minimal panel is applicable in a more heterogeneous mixture (i.e. more than two cell types are possibly present), when the single investigated region is known to be exclusively accessible in one particular cell type, while it is in the opposite state in all other cells. In this latter case and when the addressed question only refers to the quantification and analysis of the presence of this particular one cell type, a single region from the large panel of regions is eligible.

It is also an alternative embodiment of the invention to base the determination of the presence of a cell type in a biological sample on a combination of different regions as described above. To increase the likelihood of a correct determination, it is preferred that the distinctive chromatin structure of several selected additional regions is investigated. It is preferred that in such a "mini panel" comprising one or more regions, additional regions are used up to a number of seven. The preferred number of regions to be added to such a mini panel, would be one or more out of the regions of the genes as described above. Especially preferred would be a combined analysis of up to two regions as described, in order to distinguish between cell types and statuses with a sufficient high level of quality of said analysis. Other preferred combination would comprise the chromatin structure analysis of 3, 4, 5, 6, 7, 8, 9, 10, 11, 12, 13, and 14 regions. Wherever in the following the invention is described specifically for a particular cell type that is detected, it is meant to also include a combination of one regions of the above panel with one or more of the regions as indicated.

Certain markers demonstrated regions of specific genes that were particularly distinctive in some cell types relative to the other cell types tested. For example, regions, in particular open chromatin regions, of as an example for 2 regions, the regions of GP9 and FCER2 are most accessible in CD19+ B cells (BCL05),
as an example for 2 regions, the regions S100P, HIPK3 are most accessible in CD15+ granulocytes (GRC01),
as an example for 1 region, the region of TM4SF19 is most accessible in CD14+ monocytes (MOC02), and
as an example for 2 regions, the regions of CD160, and LDB2 are most accessible in CD56+ natural killer cells (NKC02) (see FIG. 5).

As a preferred example, the regions of the two genes S100P and HIPK3 thus can be used in order to distinguish between CD15+ granulocytes and the other immune cells as described above. Similarly, CD160 thus can be used in order to distinguish between CD56+ natural killer cells and the other immune cells as described above (see FIG. 5).

The present invention may further be described in certain embodiments as a kit for use in determining the presence or status of a cell in a biological sample through testing of a biological sample. A representative kit may comprise one or more nucleic acid segments as described above that selectively hybridize to the DNA of at least one of the above regions, and a container for each of the one or more nucleic acid segments. In certain embodiments the nucleic acid segments may be combined in a single vial. In further embodiments, the nucleic acid segments may also include a pair of primers for amplifying the target region. Such kits may also include any buffers, solutions, solvents, enzymes, nucleotides, or other components for hybridization, amplification or detection reactions. Preferred kit components further preferably include reagents for methylation analysis, reverse transcription-PCR, in situ hybridization, Northern analysis, restriction polymorphism analysis (RPA), DNAse I digestion, ChIP Chip®, chromatin immunoprecipitation microarray, quantitative PCR analysis, selective precipitation or conversion of cytosines with bisulfite, or combinations thereof. Preferred kits may also include any other components for determining the chromatin structure of at least one of the genes selected from the group of CD3, FOXP3, GLNY, CCR6, CAMTA1, GP9, FCER2, S-100-P, HIPK-3, TM4SF19; CD160 antigen precursor, LDB2, CD19 and GAPDH.

The kits according to the present invention may also contain: 1. Chemicals (bisulfite, etc.) for processing the cell samples; 2. Procedure protocols; 3. Oligonucleotide probes, amplicons, blockers or extension primers according to the present invention that will detect marker regions relevant to a particular cell type or status. The oligonucleotides would be constructed to generate a signal on a commonly available detection platform, such as Real Time-PCR (RT-PCR) or Single Base Extension (SBE). Each signal indicates the level of methylation at a particular target site in the sample. As an alternative, probes according to the described nucleic acids could be produced for usage on a chip; 4. A bioinformatic tool to process the results. This, e.g., software might normalize the signals from the raw data, contain a result matrix for interpretation of the read-out, or implement various algorithms that calculate, for example, cell type proportions, or potency predictions.

Another preferred aspect of the present invention relates to a kit for identifying a specific type and/or state of a mammalian cell in a sample obtained from a mammal comprising materials for performing a method according to the present invention. In one preferred embodiment according to the present invention, the kit comprises a) a bisulfite reagent, and b) materials for the methylation analysis of CpG positions in the regions of interest. The person of skill will furthermore be able to select materials for specific subsets of CpG positions in order to minimise the amount of sites to be analyzed. The kit can be a diagnostic kit.

The data as generated in the context of the present invention shows that DNA accessibility to bisulfite conversion in the CD3 gene defines CD3 expressing T-lymphocytes, as much as Foxp3 accessibility defines Tregs (Huehn, J., J. K. Polansky, and A. Hamann, *Epigenetic control of FOXP3 expression: the key to a stable regulatory T-cell lineage?* Nat Rev Immunol, 2009. 9(2): p. 83-9), since the observed correlation coefficient of above 0.8 equals the specificity of the Foxp3 TSDR to Tregs. Remaining result variability between FACS and epigenetic measurements may be attributed in part to systematic variations, including lacking precision in defining the general leukocyte count by flow cytometry. Since flow cytometric cell counting was performed about 6 hours after blood draw and epigenetic analyses one year later, the inventors propose that retrospective analyses of frozen blood samples become feasible using epigenetic immuno-phenotyping. Expression of granulysin is a functional characteristic of cytotoxic T and NK cells, which has been reported to be impaired during cancer development (Kishi, A., et al., *Differential expression of granulysin and perforin by NK cells in cancer patients and correlation of impaired granulysin expression with progression of cancer.* Cancer Immunol Immunother, 2002. 50(11): p. 604-14) and has been suggested to correlate with the prognosis of tumour patients (Galon, J., et al., *Type, density, and location of immune cells within human colorectal tumors predict clinical outcome.* Science, 2006. 313(5795): p. 1960-4). The data according to the invention shows that accessibility to bisulfite conversion of the granulysin gene is an intrinsic property of CD3−CD56+ NK and CD+CD56+ NKT cells that correlates to the amount of NK and NKT cells in whole blood as detected by flow cytometric analysis. Thus, and despite the fact, that epigenetic accessibility of the granulysin gene is also shared by a fraction of cytotoxic T cells, this epigenetic marker appears to be a good indicator for a NK cell led immune reactions. In order to further enable epigenetic immune phenotyping, the inventors developed a general standard system for whole cell counting. Equally to mRNA and certain protein technologies the inventors used a housekeeping gene, the regulatory region of GAPDH, as normalizing standard. High conservation, putative functional non-redundance and structural similarity to the cell specific epigenetic marker systems—i.e., presence of potentially differential bisulfite convertibility—were the criteria for this selection. The inventors show that the GAPDH is fully accessible in all living cells, and can therefore be used to determine the overall cell count. To warrant equimolarity of the standardisation process, the inventors have cloned the TpG variants of FOXP3, CD3, GNLY and GAPDH on a single plasmid. Accordingly, quantification becomes fully comparable, regardless of which cell type should be quantified. The inventors thus provide an integral standard system with which all cell specific parameters can be normalized equally and thus also related to each other.

When the inventors compared the infiltration of immune cells between healthy and tumour tissues, for all three unrelated tumour entities a dramatic increase of Treg numbers is found. For both lung and colorectal cancers, about a doubling of Tregs is observed, and in ovarian tissue the increase is more than 10 fold. In lung and colorectal tumours, the inventors also found a statistically significant reduction of the overall T-lymphocyte counts compared to healthy tissue. Both decrease of CD3 cells and increase of Tregs are in agreement with the pathological inability of the body to appropriately counter tumour development. This view is supported by the fact that the relative amount of Tregs within the CD3 cell compartment behaves equal for all three tumour entities, despite the vastly different cell counts in ovarian compared to lung and colorectal tissue. The observed average increase in lung, colon and ovarian cancer compared to the respective healthy tissues for the relative Treg to overall T cell ratio is at 2.5, 2.8 and 5.4 fold, respectively. For the matched pair analysis, possible only in bronchial and colorectal tissues, the inventors find app. 95% and 81% of the measured pairs (43 out of 46 pairs and 39 out of 48, respectively) show an increase in the bronchial tumour compared to the healthy adjacent tissue and more than in the colorectal cancer samples. Since sample quality of colorectal tissue was comparably low, one can argue that the differences in the matched pair analysis stems from variances in tissue quality rather than from a biological phenomenon. Thus, the data suggest a remarkable disturbance and a consistent shift of the Treg ratios in all three tumour entities. Taken together with the accepted high specificity of FOXP3 TSDR assay for the measurement of Tregs, the inventors considered this dysbalance an essential determinant rather than a bystander effect of the development of solid tumours. Thus, the data portend that the ratio of the tolerogenic-to-effector immune system may also be a strong candidate for a targeted anti-tumour strategy, whereupon it is important to consider that the known surface markers may not be the ideal candidates since they deplete both activated effector and regulatory T cells. It is further observed that tissue infiltration of all three measured cell subpopulations is significantly higher in lung and colon than in ovarian tissue. Overall this is both true for healthy and tumour tissue. However, while healthy ovarian tissue has extremely low lymphocyte counts (app. 15× less Treg, 7.5× less CD3 cells, and 10 times less granulysin cells when compared to bronchial cancers), in tumour tissues, the difference is significantly lower (3× less Treg, 2.8× less CD34 cells and 3.5× less granulysin positive cells, when compared to bronchial cancers). The low lymphocyte count in healthy ovaries is likely due to significantly low vascularization, compared to lung and colon, which are highly vascularized already in the healthy states. The observed adaptation within the tumour tissue, suggests that vascularisation in ovaries significantly changes tissue composition, while this is not true for either lung or colorectal tissue, which overall appear to have a stable vascularisation. The relative decrease of CD3 and granulysin positive cells further support the view that the immune system is repelled during tumourgenesis and only a very limited adaptive and innate immune response is mounted, with the increasing immune cell count in ovarian cancer credited to vascularization rather than an increased immune response. The data corroborate various previous reports that indicated that an increased number of CD3 positive cells is advantageous to effectively counteract tumours and thus leads to a better prognosis when tested in a univariate analysis. The inventors also show that this trend is independent of the particular tumour entity. Thus, the data support the notion that an enhancement of the adaptive immune response appears to be a useful anti-tumour approach. Despite dramatic influence of the Treg proportion and the Treg to CD3 ratio in tumour tissues when compared to healthy tissue of the same organ, the inventors did not see an inverse relation between Treg count and survival as had been reported previously. Instead, a statistically non-significant, but clear trend for a survival benefit of tumour patients with higher Treg levels was found compared to patients with lower Treg counts in two studies with 110 ovarian and 86 colorectal cancer patients. This trend is more significant for ovarian cancer, where both Treg count and Treg to CD3 cell ratio point to a better survival for patients with higher Tregs. The data for colorectal cancer are more ambiguous, and only a slight trend is observed for the overall Treg count, and no trend at all is observed for the ratio of Treg to CD3.

Combining the different datasets uncovers an intrinsic difficulty for the previously reported correlation: the inventors observe a direct linear correlation between Treg number and the overall T-lymphocytes count in all healthy and tumorous tissues. Although this direct correlation is varying in strength and ranges from 0.325 for colorectal cancer to 0.76 in ovarian cancers, it is statistically significant for all healthy and diseased tissues. Therefore, it is not plausible to assume that an increasing CD3 level and, at the same time, decreasing Tregs leads to an improved outcome—at least not if tested univariately as had been done in previous studies. However, differing results between the present and previous data also require also functional and technical explanations. With respect to this, epigenetic counting usually is a relative and three dimensional measures, whereas cell counting of absolute cell numbers regardless of overall cell density in tissues. In this case, the previous data may correlate higher Treg counts that are due to higher tumour cell density. Also, higher density of Tregs may occur in particular areas of the tumour, a phenomenon that epigenetic studies cannot pick up. Biologically, Treg counts were conducted by counting cells that express Foxp3. It is now known that the specificity of Foxp3 expression to Tregs is limited, since activated effector T cells also express Foxp3, while these cells do not have an accessible FOXP3 TSDR. It is thus feasible that a low number of activated effector T cells correlates to improved outcome.

Taken together, the inventors believe that epigenetic immuno-phenotyping according to the present invention is a novel method that may add new comparability and ease to immuno-phenotyping in blood and, possibly more importantly, in solid tissues. Due to its relative robustness, this may also be the better method for clinical routine measurements, where requirements for good laboratory practice is difficult to achieve. However, before this technology can readily be applied to address immunological questions in solid tissues and blood, a major and orchestrated effort to discover novel and specific immune cell markers equivalent to CD3 or FOXP3 and standardizable as shown on GAPDH according to the present invention to provide a widely comparable standard system is imperative. Biologically, the data presented here firmly establish an outstanding role of CD3 and, in particular, Tregs in tumour development. Despite the doubtful prognostic significance of Treg, the present inventors argue that the dramatic Treg increase in all tumours is not an unfortunate bystander effect, but instead is a required prerequisite for successful tumour establishment. The inventors thus suggest that Treg ought to become a prime target for anti-tumour strategies, although such drugs should probably be designed to act not necessarily systematic but rather specific in the tumour microenvironment. All current data support an important role of CD3 cells in anti-tumour responses. However, the inventors regard the association of Tregs to CD3 cell counts as a severe inhibition to the efficacy of T cell based drugs, since an unselected homing of CD3 cells without an inhibition of Treg homing threatens to always co-attract activator and its suppressor alike.

In the context of the present invention, it could thus further be shown that promoters, promoter-proximal regions or coding sequences of particular genes show a cell type- or state-specific chromatin structure. The inventors revealed gene regions that behave principally similar to what is stated above for T cell differentiation and the immune status. In particular, a number of fourteen gene regions have been discovered that are sensitive indicators of cell type/status depending on their degree of chromatin accessibility as exemplified by their resulting accessibility to conversion of cytosine to uracil during bisulfite treatment. The accessibility translated into an epigenetic epiphenotype of these regions that are found to be variable between cell types, but maintain a consistent phenotype within cell types. They have been validated on multiple samples of each cell type and will serve as marker regions that can be specifically targeted in assays to determine cell identity, status, purity and potency. Furthermore, they are indicators of essential changes in cellular character and thus are useful in tissue engineering and for monitoring compounds that effect such changes. The inventors describe a series of genetic regions as described herein whose accessibility of chromatin and epigenetic (e.g. methylation) patterns are statistically correlated to the type or status of a cell. As such, these regions represent particularly sensitive and useful marker regions for distinguishing cell type.

The present invention shall now be described further with reference to the accompanying examples, nevertheless, without being limited thereto. For the purposes of the present invention, all references as cited herein are incorporated by reference in their entireties. In the Figures and the Sequence Listing, FIG. 1 shows the A) Genomic organization and localisation of the genes CD3, GNLY and GAPDH. Transcripts are shown depending on the direction above or below the chromosomal bar. Amplicons aligning to the various gene regions are indicated. B) Epigenetic profiling of selected amplicons. The results from bisulfite sequencing are indicated in a colour coded matrix, where each line represents the sequencing data in a cell type and each block represents an amplicon. Black corresponds to DNA that is inaccessible to conversion by bisulfite and gray corresponds to DNA that is accessible to bisulfite conversion.

Figure 2:
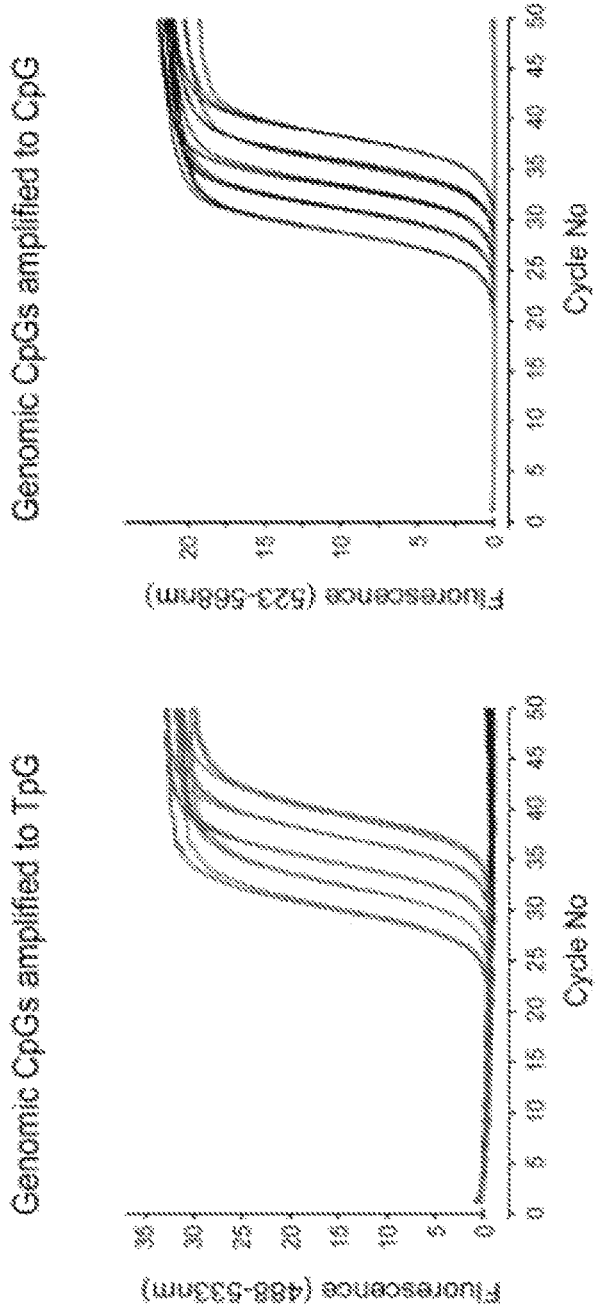
Figure 2:
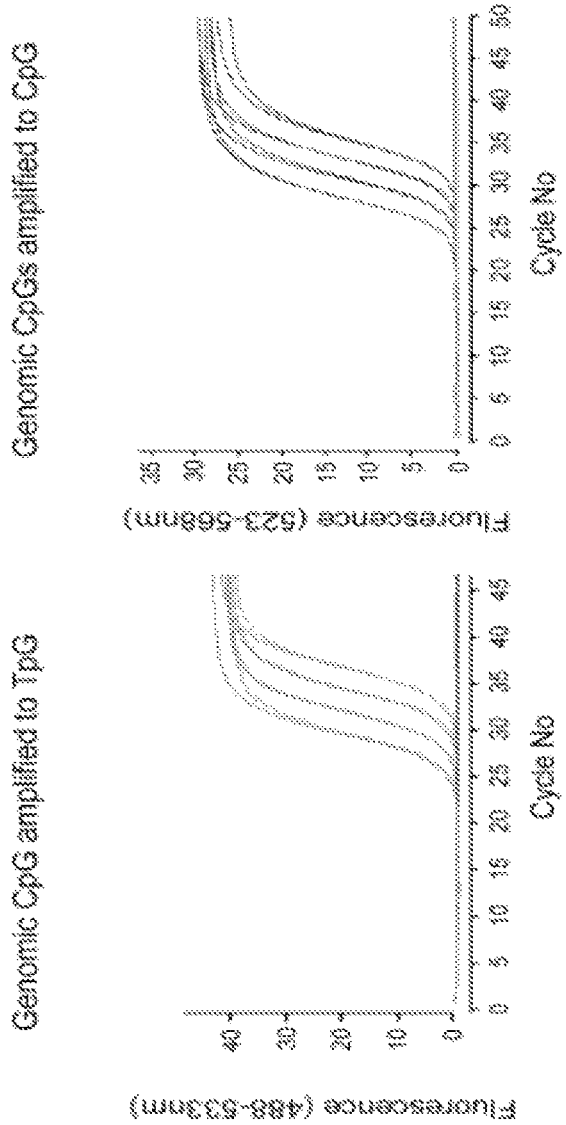
Figure 2:
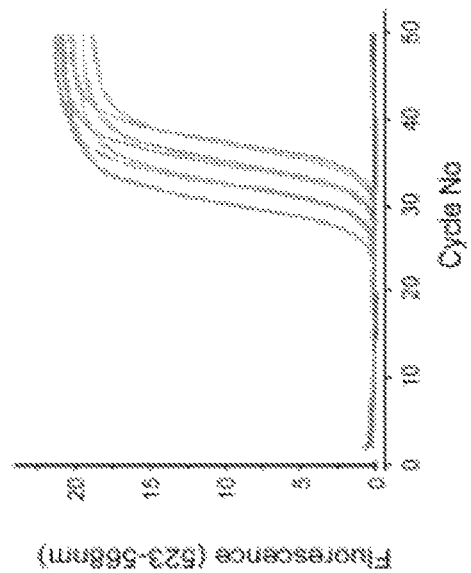
Figure 2:
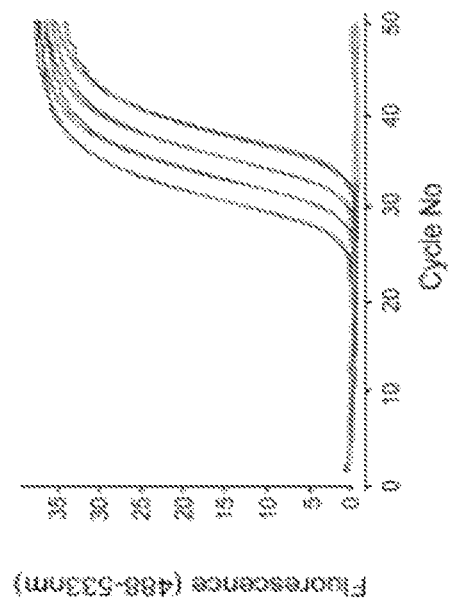

FIG. 2 shows amplification profiles of the specific RT PCR assays. Each time, in the left panel the PCR system using the primers and probes for fully bisulfite converted DNA is shown, while in the right panel the version for DNA with CpGs inert to bisulfite conversion is demonstrated. Linearity of all PCR systems is shown inside of each graph by plotting measured CP values over the log concentration of template used.

Figure 3:
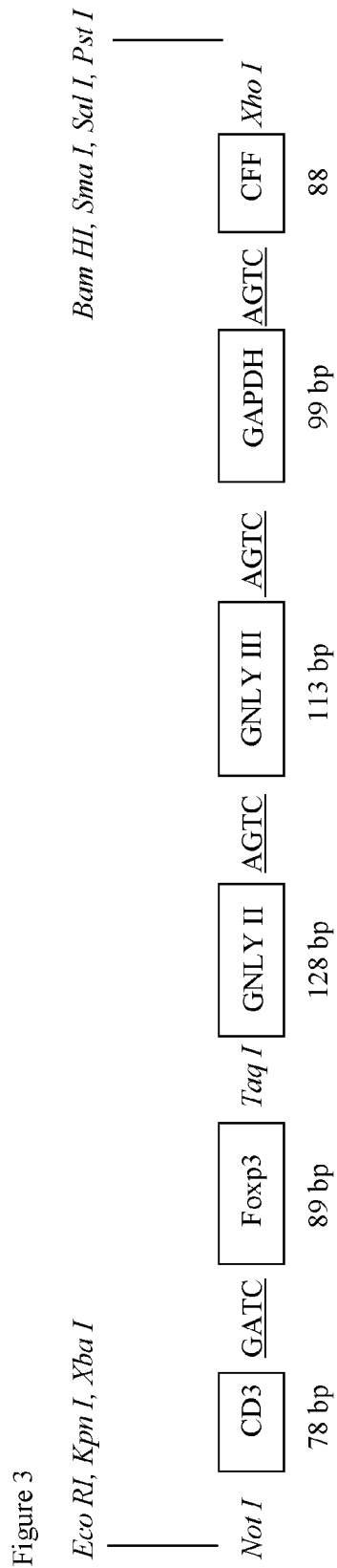

FIG. 3 shows a preferred embodiment of the fully bisulfite converted control plasmid according to the examples below.

Figure 4:
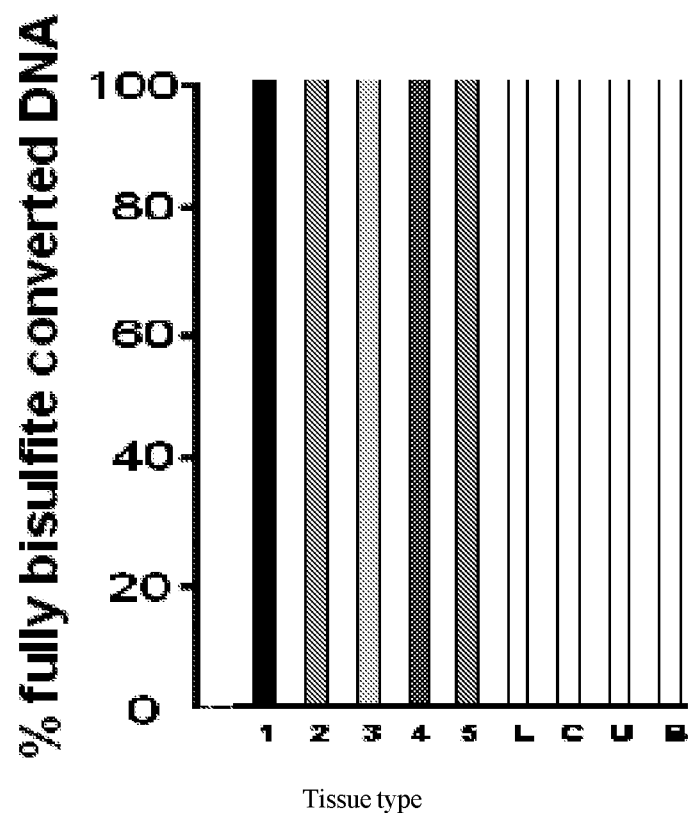

FIG. 4 shows the ratio of GAPDH fully bisulfite converted DNA versus only partially bisulfite converted DNA in a variety of cells and tissues (1. Granulocytes, 2. Monocytes, 3. NK cells, 4. CD4 naïve cells, 5. CD8 cells, L. Lung, C. colon, U. uterine tissue, B. breast tissue. The inventors could never detected a signal for only partially converted DNA. Therefore, all cells appear to contain only fully accessible DNA, i.e. open chromatin.

Figure 5:
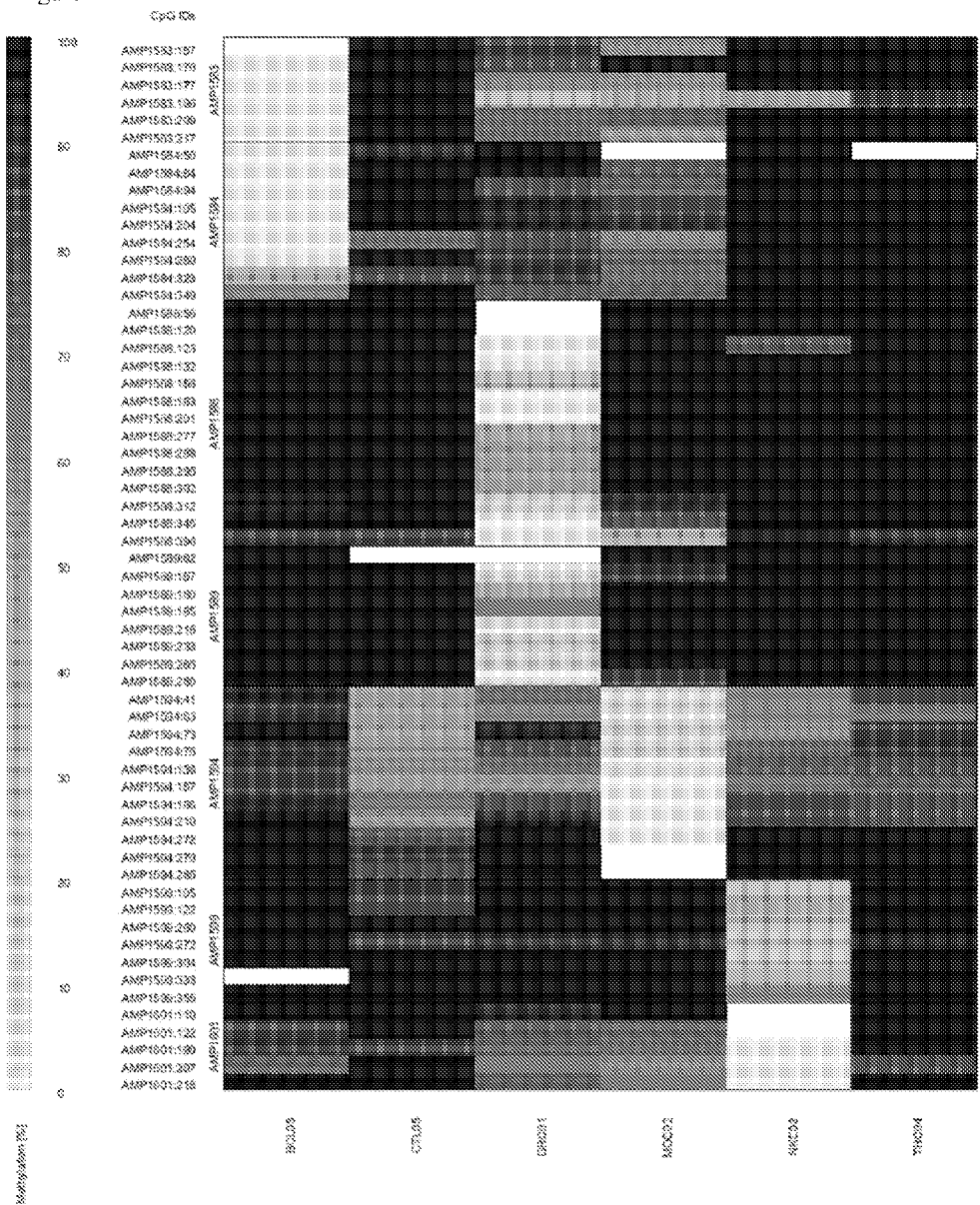

FIG. 5 shows the methylation analysis-based chromatin accessibility analysis of certain preferred cell type and/or status specific genes. The cell types are BCL05: CD19+ B cells; CTL05: CD3+ CD8+ cytotoxic T cells; GRC01: CD15+ granulocytes; MOC02: CD14+ monocytes; NKC02: CD56+ natural killer cells; and THC04: CD3+ CD4+ helper T cells. The regions/genes tested are

| AMP-ID/SEQ ID No. | Gene Name/Gene-ID |
|---|---|
| 1583/16 | Platelet glycoprotein IX/ENSG00000169704 (GP9) |
| 1584/17 | Low affinity immunoglobulin epsilon Fc receptor/ENSG00000104921 (FCER2) |
| 1588/18 | Protein S100-P (S100 calcium-binding protein P)/ENSG00000163993 |
| 1589/19 | Homeodomain-interacting protein kinase 3/ENSG00000110422 (HiPK3) |
| 1594/20 | Transmembrane 4 L6 family member 19/ENSG00000145107 (TM4SF19) |
| 1599/21 | CD160 antigen Precursor (Natural killer cell receptor BY55)/ENSG00000117281 |
| 1601/22 | LIM domain-binding protein 2/ENSG00000169744 (LDB2) |

The CpG positions as analyzed in the actual amplicon are indicated by the numbers following the amplicon number.

Figure 6:
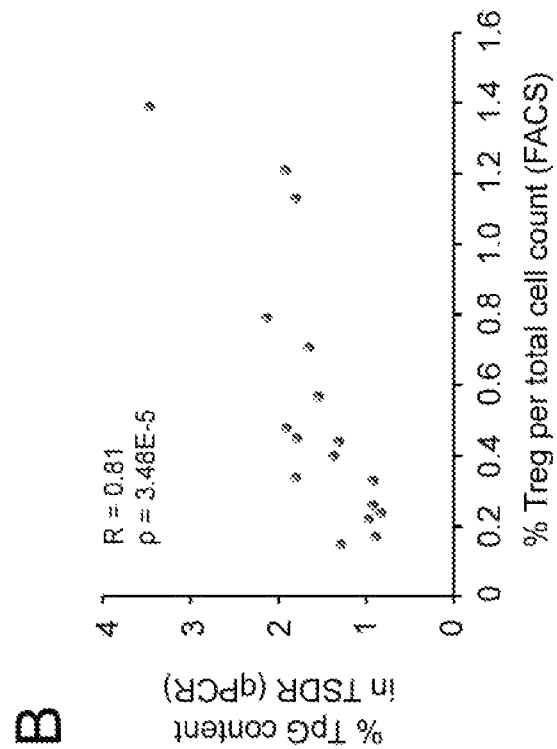
Figure 6:
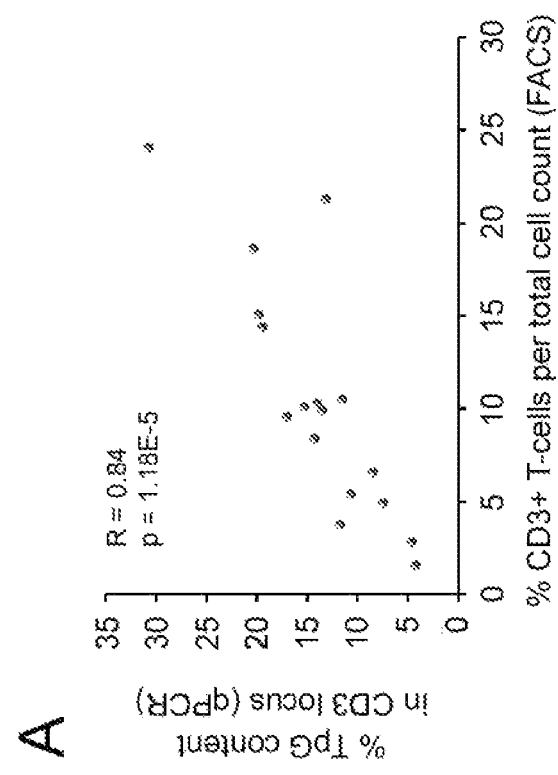
Figure 6:
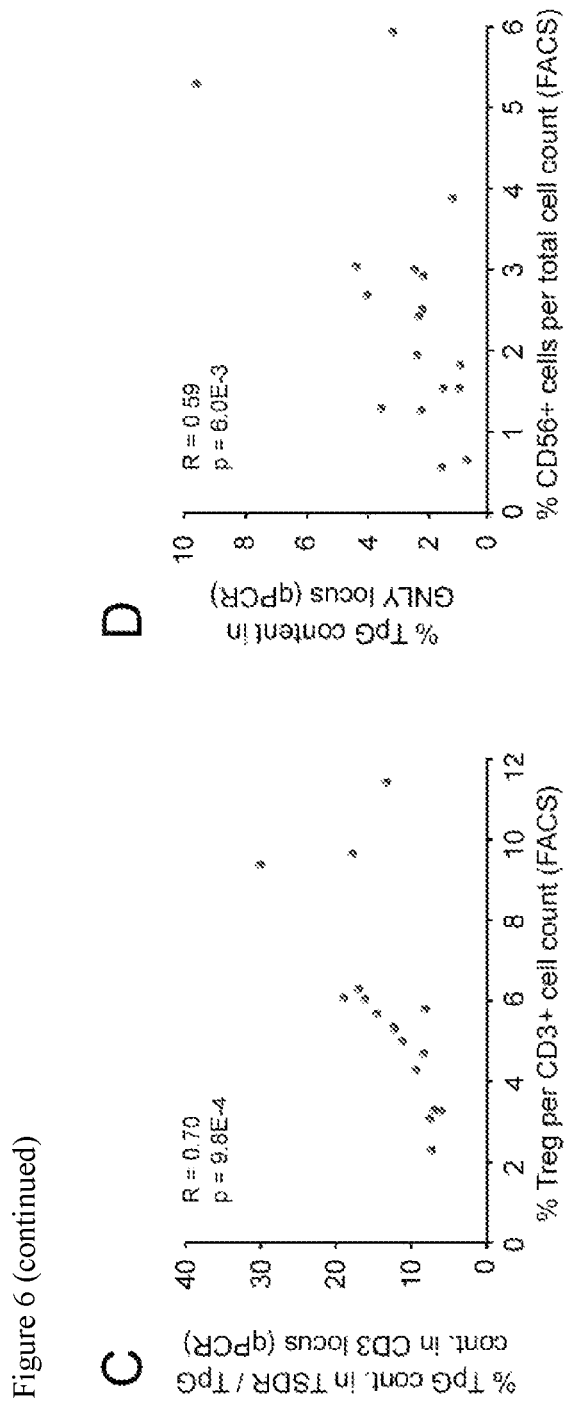

FIG. 6 shows the analysis of peripheral blood from ovarian cancer patients before and after treatment with Catumaxumab (see examples, below). Measurements were conducted for all available blood samples using FACS sorting selecting either for CD3+ cells versus all nucleated cells (A), CD4+CD25+CD127− versus all nucleated cells (B), CD4+CD25+CD127− versus CD3+ cells (C) and CD56+ cells versus all nucleated cells (D). FACS results in percent [%] are plotted on the X-axis and compared to the percentage that resulted from the epigenetic analysis of cells by means of qPCR which is plotted on the Y-axis. R indicates the Pearson correlation coefficient for each FACS to the epigenetic measurement. The p-values indicate the statistical significance of the correlations.

Figure 7:
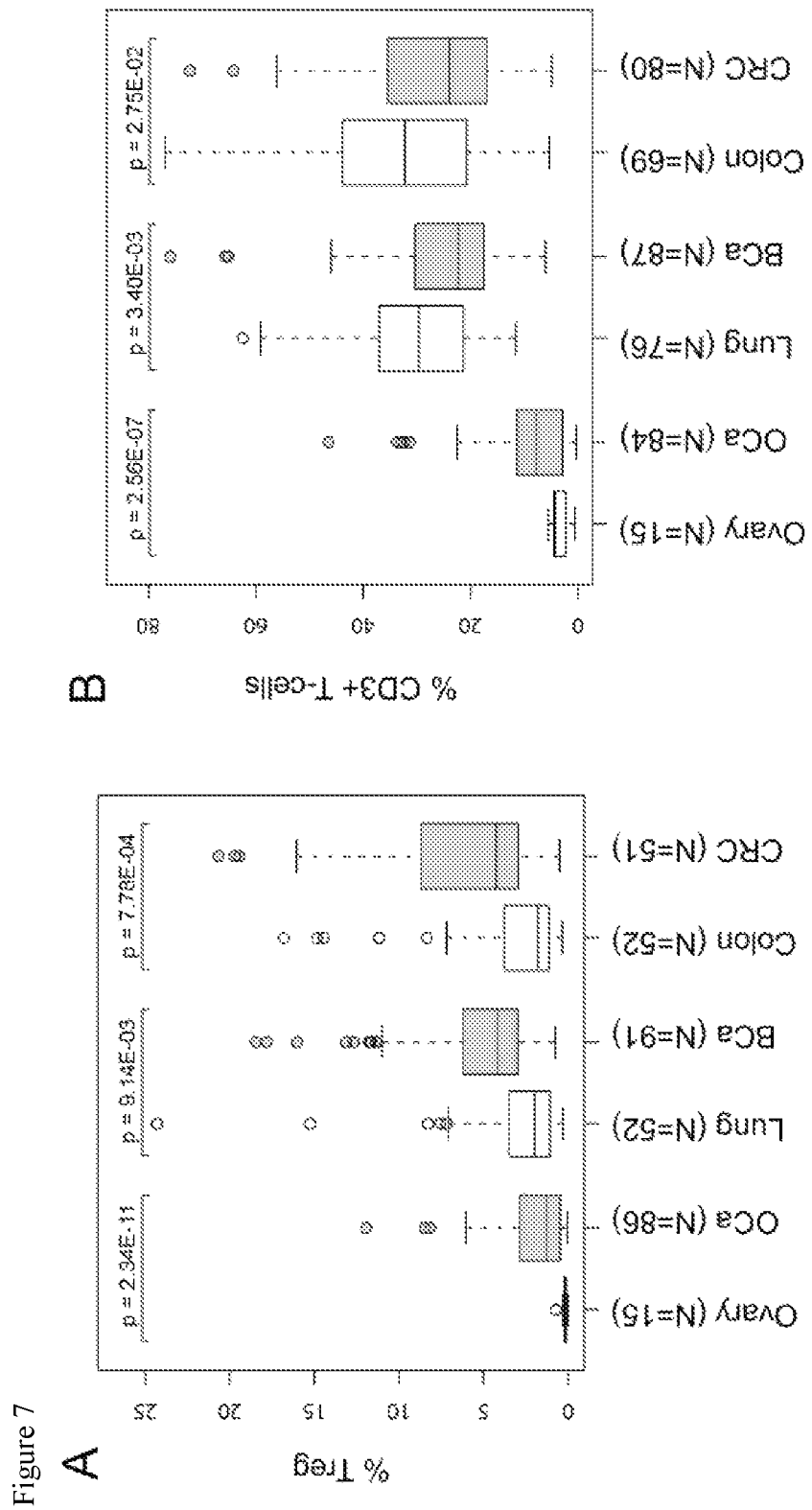
Figure 7:
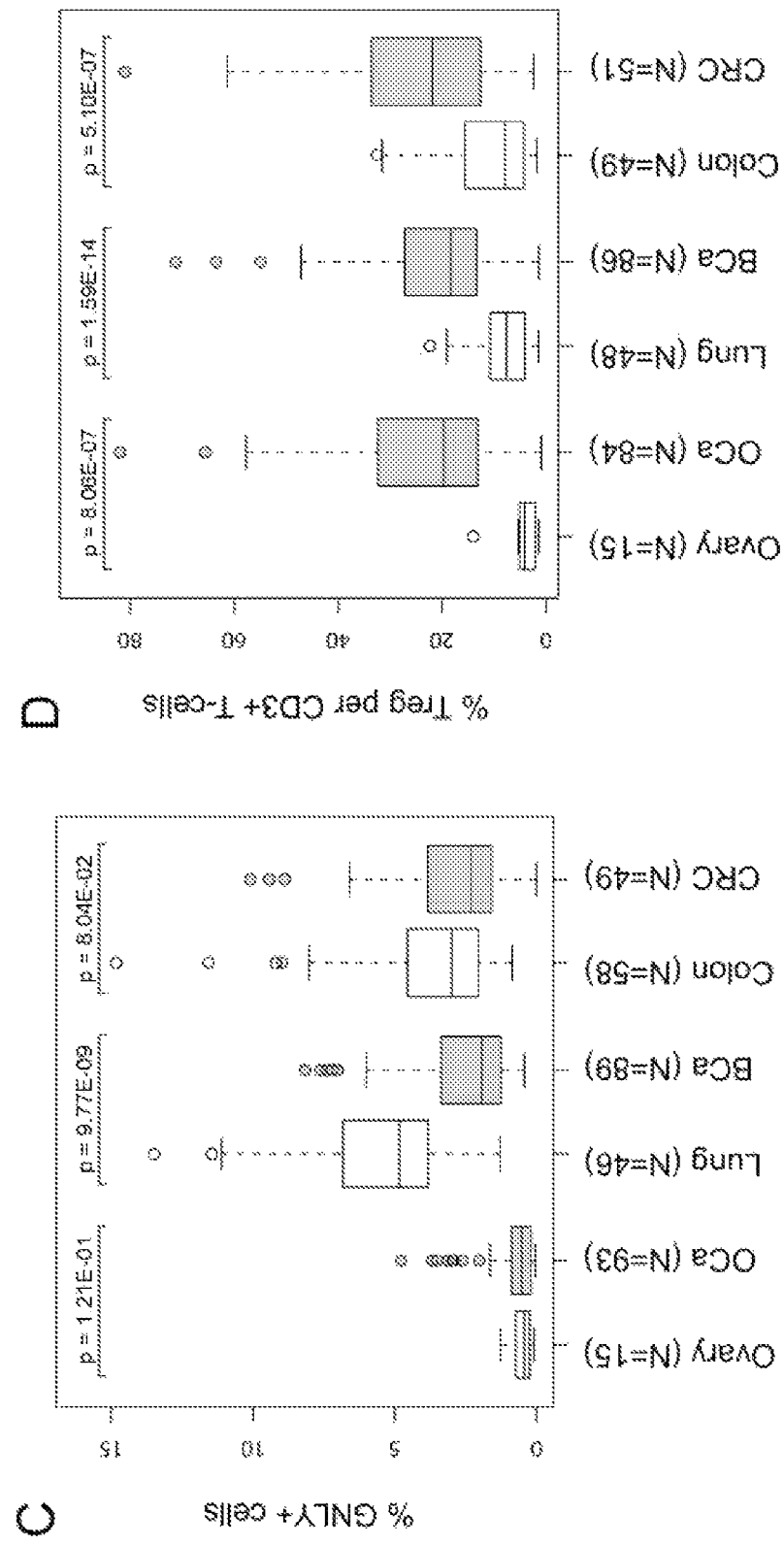

FIG. 7 shows tissue infiltrating lymphocytes in healthy and cancerous tissue. Boxplots showing the relative abundance in percent of the total cell count of A) Tregs, B) $CD3^+$ T cells, C) $GNLY^+$ cells and D) Tregs within the CD3 compartment in healthy and cancerous ovarian (OC), lung (BCa) and colorectal (CRC) tissues. N indicates the number of patients included in each boxplot. The box in the middle depicts 50% of the distribution. The central line in the box represents the median of the distribution, and the whiskers cover 95% of all measured data. Outliers from this distribution are indicated by circles. The indicated p-value were obtained from the two-sided, heteroskedastic students t-Test.

SEQ ID No 1 shows the DNA sequence of the insert as cloned into the plasmid as used in the examples.

SEQ ID No 2 to 15 show sequences of the primers as used in the experiments that are specific for bisulfite-converted DNA.

SEQ ID No 16 to 22 show sequences of the amplicons as analyzed in FIG. 5.

SEQ ID No 23 to 29 show sequences of the regions of interest which also can be analyzed in the context of the invention. The ROIs correspond to AMP1583, AMP1584, AMP1588, AMP1589, AMP1594, AMP1599, and AMP1601, respectively.

EXAMPLES

Materials and Methods
Abbreviations:
Amp, amplicon; CD3D, T-cell surface glycoprotein CD3 delta chain; CD3G, T-cell surface glycoprotein CD3 gamma chain; FOXP3, Forkhead box protein P3; GAPDH, Glyceraldehyde-3-phosphate dehydrogenase; GNLY, Granulysin.

Cells and Tissue Samples

Formalin-fixed and paraffin-embedded tissue samples were retrieved from the archives of the Institute of Pathology, Charité—Universitätsmedizin Berlin, Campus Benjamin Franklin. Representative paraffin blocks of tumour and normal tissue were selected and tissue microarray (TMA) of the colorectal or bronchial carcinoma specimens with the corresponding normal parenchyma were constructed using cores of 1 mm in diameter. Fresh frozen ovarian tissue samples and blood were retrieved from the tumour bank ovarian cancer, Charite—Universitätsmedizin Berlin, Campus Virchow.

Isolation of Genomic DNA

For purification of genomic DNA from human blood, tissues, the DNeasy Blood and Tissue Kit (Qiagen, Hilden, Germany) was used. In case of ascites the inventors followed the protocol for isolation of total DNA from cultured cells. Genomic DNA from formalin-fixed paraffin-embedded (FFPE-) tissues samples was isolated using the QIAamp DNA FFPE Tissue Kit (Qiagen, Hilden, Germany). Paraffin blocks were trimmed to remove excess of paraffin and tissue section thickness was adjusted to 10 um. Each reaction was carried out using 10 tissue sections.

Sodium Bisulfite Conversion of Genomic DNA

Sodium bisulfite-mediated conversion was performed applying the EpiTect Bisulfite Kit (Qiagen, Hilden, Germany) and reactions were carried out using 0.5 to 1 ug of purified genomic DNA. In brief, thermal cycling of genomic DNA under high bisulfite salt concentrations and low pH lead to the conversion of unmethylated cytosine residues into uracil (which is replicated as thymine in a subsequent PCR). As under these conditions methylated cytosines (as found in the context of CpG dinucleotides) remain unchanged, the treatment translates epigenetic marks into sequence information.

Oligonucleotides

Oligonucleotides such as amplification primers and hydrolysis probes used in this work are indicated by their chromosomal positions relative to the assembly of the human genome GRCh37 (e!Ensemble release 56; September 2009).

Oligonucleotides for quantitative bisulfite sequencing: a) intergenic CD3G (ENSG00000160654)/CD3D (ENSG00000167286) region: Amplicon No. 1, forward primer: 11:118213200-118213221:1, reverse primer: 11:118213616-118213637:1; amplicon No. 2, forward primer: 11:118214271-118214292:1, reverse primer: 11:118214685-118214705:1; amplicon No. 3, forward primer: 11:118214702-118214723:1, reverse primer: 11:118215151-118215173:1; b) GNLY (ENSG00000115523) gene region: Amplicon No. 1, forward primer: 2:85921382-85921404:1, reverse primer: 2:85921742-85921763:1; amplicon No. 2, forward primer: 2:85921807-85921828:1, reverse primer: 2:85922259-85922279:1; amplicon No. 3, forward primer: 2:85922895-85922916:1, reverse primer: 2:85923327-85923348:1; c) GAPDH (ENSG00000111640) CpG island: Amplicon No. 1, forward primer: 12:6644119-6644135:1, reverse primer: 12:6644635-6644656:1; amplicon No. 2, forward primer: 12:6643586-6643604:1, reverse primer: 12:6643990-6644011:1.

Oligonucleotides for real-time PCR based assays: a) FOXP3 (ENSG00000049768) TSDR: methylation-specific PCR: forward primer: X:49117219-49117246:1, reverse primer: X:49117283-49117307:1, probe: X:49117256-49117273:1; demethylation-specific PCR: forward primer: X:49117219-49117246:1, reverse primer: X:49117283-49117307:1, probe: X:49117256-49117278:1. b) CD3: methylation-specific PCR: forward primer: 11:118213633-118213653:1, reverse primer: 11:118213686-118213707:1, probe: 11:118213670-118213687:1; demethylation-specific PCR: forward primer: 11:118213632-118213653:1, reverse primer: 11:118213686-118213709:1, probe: 11:118213664-118213690:1. c) GNLY: methylation-specific PCR: forward primer: 2:85921878-85921895:1, reverse primer: 2:85921964-85921992:1, probe: 2:85921918-85921943:1; demethylation-specific PCR: forward primer: 2:85921877-85921895:1, reverse primer: 2:85921964-85921992:1, probe: 2:85921911-85921939:1. d) GAPDH: demethylation-specific PCR: forward primer: 12:6644378-6644399:1, reverse primer: 12:6644456-6644476:1, probe: 12:6644429-6644457:1.

The sequences of the primer as used specific for bisulfite-converted DNA are as follows (see, for example, FIG. 5):

| Amplicon/SEQ ID No | Orientation | Sequence |
| --- | --- | --- |
| AMP1583-2 | Reverse | CTTCTCTAAACCCAACATCAAT |
| AMP1583-3 | Forward | GAATTTAGGAGGTAGAGGTGGT |
| AMP1584-4 | Reverse | GGATATTTGATTTGGGAGTTTA |
| AMP1584-5 | Forward | AACCACTAACAACTTCTATTTTCA |
| AMP1588-6 | Reverse | TTTTGTGTTAATATGAGGTTGTTT |
| AMP1588-7 | Forward | ACCCTCTCCCTACTCAAATACT |
| AMP1589-8 | Reverse | AGTGGTATAATTTTGTTTTGATTTT |
| AMP1589-9 | Forward | AAATTCTCATCCTCCCACTAA |
| AMP1594-10 | Reverse | ACCCACAAACCTACATTAAAAA |
| AMP1594-11 | Forward | GTAAGGAGAGTGATGAGGAAAA |
| AMP1599-12 | Reverse | CAATTCACAAATCCCATAAATA |
| AMP1599-13 | Forward | TTGTTTAGGTGAGGATAGGTTT |
| AMP1601-14 | Reverse | AGGTATTTTAAGGGTTTGAATG |
| AMP1601-15 | Forward | TCTCCTCACAATCTAACAAAAA |

Quantitative Bisulphite Sequencing

Targeted regions were pre-amplified from 7 ng sodium bisulfite converted genomic DNA using bisulfite-conversion specific primers. PCR was performed in a final volume of 25 µl containing 1×PCR Buffer, 1 U Taq DNA polymerase (Qiagen, Hilden, Germany), 200 µM dNTP, 12.5 pmol each of forward and reverse primers. Thermocycling was performed at 95° C. for 15 min, followed by 40 cycles of 95° C. for 1 min, 55° C. for 45 s and 72° C. for 1 min, and a final extension step of 10 min at 72° C. The PCR product was purified using ExoSAP-IT (USB Corp.) and directly sequenced applying the amplification primers and the ABI Big Dye Terminator v1.1 chemistry (Applied. Biosystems). Products were purified by Ethanol precipitation, dissolved in 1M betain and subjected to capillary electrophoresis on an ABI 3100 genetic analyzer. AB1 files were interpreted using ESME, which normalizes sequence traces, corrects for incomplete bisulphite conversion and allows for quantification of methylation signals at CpG sites.

Real-Time PCR

Real-time PCR was performed using Roche LightCycler 480 Probes Master chemistry (Roche Diagnostics) in a final reaction volume of 20 µl containing 30 pmol each of methylation- or demethylation-specific forward and reverse primers, 5 pmol of hydrolysis probe, 50 ng of □-phage DNA (New England Biolabs), and 60 ng of bisulfite-converted genomic DNA template or a respective amount of plasmid standard. Each sample was analyzed in triplicates using a LightCycler 480 System (Roche). For all assay systems cycling conditions included a 95° C. preheating step for 10 min followed by 50 cycles of 95° C. for 15 s and 1 min at 61° C. CP ("crossing point") values were computed by the second-derivative maximum method applying the LC480 analysis software and template copy numbers were calculated from calibration curves (using serial dilutions of appropriate plasmid-based standards) by linear regression.

Plasmid Standard

Bisulfite-converted methylated, and bisulfite-converted demethylated target regions for the various real-time PCR based assays were designed in silico, synthesized (Genscript Inc.) and fragments were inserted into plasmid pUC57. Recombinant plasmids were linearized and serially diluted in 10 ng/µl of λ-phage DNA (New England Biolabs) to obtain standards for real-time PCR based assays with final concentrations of 12,500, 2500, 500, 100, 20 and 4 template copies per reaction.

Cell Sorting of Major Peripheral Blood Leukocyte Population

Peripheral blood samples were obtained from healthy donors after informed consent in accordance with local ethical committee approval. Fractionation of blood samples into different leukocyte populations such as granulocytes (CD15+), monocytes (CD14+), CD4+ T cells (CD3+CD4+), Treg (CD4+CD25$^{high}$CD45RA−), B cells (CD19+), NK cells (CD56+, CD56$^{bright}$, CD56$^{dim}$), naive CD8+ T cells (CD3+CD8+CD45RA+CD127+) and memory CD8+ T cells (CD3+CD8+CD45RA−CD127+/−) was performed as described previously (Baron et al. Eur J Immunol). Purities of sorted cells were >97% as determined by flow cytometry and viabilities were always >99%.

Statistical Analysis

Amounts of methylated (CpG variant) and unmethylated (TpG variant) DNA were estimated from calibration curves by linear regression on crossing points from the second-derivative maximum method. The median was used to aggregate triplicate measurements of the tested samples. The proportion of gene specific DNA was computed as the ratio of the gene specifically TpG variant DNA and either the sum of the TpG and CpG variants of this same gene or the number of GAPDH TpG variant copies. Cumulative survival was calculated by the Kaplan Meier method using SPSS. The univariate comparison between groups, statistical significance was assessed using the Cox-Mantel test. For correlation analysis, Pearson's product moment coefficient, or Spearman rank correlation and t test statistics were used. All P values are two-sided.

Results

Certain specific genes as mentioned herein were analyzed that were identified by the present inventors as fully converted by bisulfite, and thus indicating an accessible chromatin structure (see FIGS. 1 to 4). Using specific RT-PCR settings, the inventors could show that amplification of DNA only occurs when a fully bisulfite converted region is present. In case of a non-converted region, no amplification products are observed.

The data in the Figures show that the established PCR systems exclusively amplify either the entirely converted, or the entirely unconverted DNA species. No cross contamination between the two species was observed.

In order to test the reverse specificity, plasmid control systems were designed that mimic bisulfite conversion, as shown in FIG. 3. The plasmid system contained all required components to quantify the amount of copies of fully bisulfite converted CD3, FOXP3, GNLY and GAPDH gene regions as analyzed in this particular setting.

The plasmid was constructed by introducing the sequence *gcggccgc*CCTAAACACTACCACATCT*CA*AAACCCCTTAAAAAAAAC*CA*T*CA*ACCCCATAA*CA*CAAAC*CA*TAACAACTAAAT-TTCT*gatc*GTTTT*TG*ATTTGTTTAGATTTTTT*TG*TTATTGA*TG*TTATGG*TG*GT*TG*GATG*TG*T*TG*GGTTTTAT*TG*ATATTA*TG*GAGGAAGAGA-AGAGG*c**tcgac*      CCAAACCCCTACCTC*CA*CATCTA*CA*TAATAAAAACCATTAACCCTCAT*CA*ATAAATCTA*CA*TTTCCT*CA*AACCTACACTAT-CTAAAATTATA*CA*AAACTAATAAAAAAACAAA-ATCTCTTCTATATTC*agtc*GGAATAGAGGAGAAG-AGAGAGTTT*CA*TTTTTTTGGTTTTTTAGAAG-GAA*CA*TGAGAATA*CA*TGTTTGTG TTGAGAGTGGGTTAGAG*CA*GTTTTAGGGTA-AAGTATGTGGATA*agtc**G*GTTTT*TG*GTAT*TG*TAGGTTT*TG*GGATGTTAGTG*TG*TAG*TG*GGTGTATTTTTGTT*TG*GATGTTG*TG*TTTG*TG*GTAGAG*TG*GT*TG*TTATGTTGTAAT*TG*G*agtc*GTTTTTTTTAAAGAGTGTTTTTGATAGGGAT-TGTTTTAGGA      ATTAGGTAGGAGAGAAGGGAG-TGTGAGAGGTGAAAGTTATTATTATT*ctcgag* (SEQ ID NO. 1) into a pUC 57 plasmid background by using the NotI-XhoI restriction sites. The asterisks designate the potential methylated sites, small letters indicate borders of the general structure of the construct NotI-CD3-FOXP3-NKII-NKIII-GAPDH-CFF-XhoI The quantification for a real time PCR assay is achieved by providing a standardizing plasmid, which is quantified by absorption measurement in nanodrop or alternative methods such as UVette analysis or Quibit system (Invitrogen), and the determination of the optical density.

Based on this measurement, a concentration of the plasmid is determined and a standard measurement row is made by the application of a serial dilution of the measured plasmid. By this means, a standard is prepared and determined (provided) that is exactly equimolar for all genes on the plasmid. While this absolute equimolarity is a preferred embodiment, and the inventors propose to use this standardization system for all samples, an analysis is also envisaged with a similar system, if various different standards are employed, which might be on different plasmids or even do not consist of plasmid or DNA standards.

Then biological samples were analyzed after initially detecting the fully bisulfite converted fraction of CD3, FOXP3, GLNY and GAPDH in the plasmid system.

Living cells are defined by the activity of so called house keeping genes, thus, these genes by definition must be active in all cells. It was shown in various experiments that all cells have a fully bisulfite accessible GAPDH locus (i.e. active). For this, the inventors analyzed granulocyte cells, monocyte cells, NK cells, CD4 naïve cells, CD8 cells as well as tissue from lung, uterus, breast and colon and showed that all the loci in the cells were entirely accessible to bisulfite conversion.

In order to test for cells that had accessible chromatin, the inventors analyzed the above PCR plasmid system that recognizes only fully bisulfite converted DNA. To show that no residual cells were present that have restricted access to bisulfite conversion, the inventors tried to amplify these cells with a system that was specific for non-fully converted DNA, and could not detect any signal in any sample.

Since approximately all possible DNA signals are derived from either fully converted or fully unconverted DNA, the total number of non apoptotic, non-necrotic cells can be reliably determined by measuring fully accessible GAPDH.

Next, DNA fragments were analyzed that are only transcriptionally active in particular cells. Again, the inventors analyzed the fully accessible DNA at these regions, and related them then to the amount of accessible GAPDH in the test plasmid construct.

To check for the accuracy of the data the inventors compared the two following analysis with each other:

% SCT1=copy FBC SPG/copy FBC GAPDH to the result of the measurement/calculation

% SCT2=copy FBC SPG/(copy FBC SPG+copy NBCSPG)

wherein

% SCT1 is the amount of the specific cell type as determined by the first method, and % SCT2 is the amount of the specific cell type as determined by the second method.

copy FBC SPG is the copy number of the fully bisulfite converted DNA of the specific gene, copy FBC GAPDH is the copy number of the fully bisulfite converted DNA of GAPDH, and copy NBCSPG is the copy number of the non bisulfite converted DNA of the specific gene.

The analyses were repeated on whole blood samples, and gave the following data:

| NK [%] when normalized to NBC NK | NK[%] normalized to FBC GAPDH |
|---|---|
| 3.5 | 3.6 |
| 5.5 | 5.3 |
| 6.4 | 6.4 |
| 7.2 | 7.6 |
| 5.3 | 5.6 |
| 7.1 | 7.2 |

Establishment of Cell Type Specific Gene Regions Susceptible for Complete Bisulfite Conversion and qPCR Assay Design Bisulfite-conversion accessibility of CpG dinucleotides in the intergenic control region of the CD3D and CD3G (chr.11q23.3) genes, granulysin gene region (Chr.2 p11.2) and the CpG island in the GAPDH gene (Chr. 12 p13.31) was tested by means of bisulfite sequencing. It was found that in the CD3 proximate region all cytosines were completely converted in naïve CD4$^+$ and CD8$^+$ T-lymphocytes (FIG. 1B) resulting in the TpG variant only. The same region is not bisulfite converted in the other tested cell types, including granulocytes, monocytes, B-lymphocytes and NK cells resulting in the "CpG variant". For the granulysin, it was found that the analyzed gene region exists exclusively in the CpG variant in naïve CD4 and CD8 T lymphocytes, monocytes, granulocytes and B-cells, while it appears to exist in the TpG variant in natural killer cells (FIG. 1B). The inventors exclusively found the TpG variant in all tested cell types in the analysed GAPDH region (FIG. 1A). Based on these data, PCR amplicons for the analyzed loci of the CD3, GNLY and GAPDH regions were designed. For each region, one PCR system was designed that exclusively recognizes the TpG variant template, and one PCR system that is specific for the CpG variant template, including a variant-specific fluorescence labelled detection probe for each assay (FIG. 2). Also a plasmid system for each of the three loci was constructed that corresponded to the TpG and CpG variants. The inventors showed high linearity of amplification over orders of magnitude (amplification efficiency ranged between 1.95 and 2). Also a high specificity was shown, since cross-reactivity with each TpG- and CpG-variant specific PCR system with the mutually opposite template was detected, even when tested at unphysiologically high concentration (copy numbers ranged from 20 to 12500 copies of plasmid DNA) (FIG. 2).

Characterization of Main Blood Cell Fractions with qPCR Assays for Cd3, GLNY and GAPDH The PCR systems for CD3, GNLY and GAPDH was tested on blood cell fractions that were purified according to the separation scheme published recently (Baron, U., et al., *DNA demethylation in the human FOXP3 locus discriminates regulatory T cells from activated FOXP3(+) conventional T cells*. Eur J Immunol, 2007. 37(9): p. 2378-89). Using serial dilutions of purified plasmids containing the equivalent of the genomic, bisulfite converted DNA regions as standard, the number of DNA copies consisting of the TpG variants was determined. As control, the CpG template variant was measured in a separate reaction. The ratio of the copies of both fractions for each gene region was calculated and is shown in Table 1.

TABLE 1

| Immune Cell Type | | CD3-Assay | | | GLNY-Assay | | | GAPDH-Assay | | |
|---|---|---|---|---|---|---|---|---|---|---|
| | | Copy number | | Ratio [%] TpG/ TpG + CpG | Copy number | | Ratio [%] TpG/ TpG + CpG | Copy number | | Ratio [%] TpG/ TpG + CpG |
| | | TpG | CpG | | TpG | CpG | | TpG | CpG | |
| Granulocytes | CD15+ | 4.3 | 1513.8 | 0.3 | 6 | 1120 | 0.5 | | 0.5 | 100 |
| Monocytes | CD14+ | 0 | 873 | 0 | 4 | 645.6 | 0.6 | | 0 | 100 |
| NK cells | CD56+ CD16+ CD3− | 2.3 | 218.8 | 1 | 240.7 | 6.1 | 97.5 | | 0 | 100 |
| NK T-cells | CD56+ CD8− CD3+ | n.d. | n.d. | n.d. | 150.5 | 6.3 | 96 | 232.1 | 0 | 100 |
| Th cells | CD4+ | 1009.4 | 1.6 | 99.8 | 11.7 | 435.7 | 2.6 | 772.7 | 0 | 100 |
| Regulatory T-cells | CD4+ CD25+ FOXP3+ | 2726.2 | 3.6 | 99.9 | 0 | 1162.7 | 0 | 2197.4 | 0 | 100 |
| Memory cytotoxic T-lymphocytes | CD8+ CD45RA− CCR7− | 488.6 | 0.8 | 99.8 | 0 | 220 | 0 | 384.5 | 0 | 100 |
| Naive cytotoxic T-lymphocytes | CD8+ CD45RA+ CCR7+ | 1859.9 | 4.3 | 99.8 | 159.4 | 614.8 | 20.6 | 1475.1 | 0.4 | 100 |
| B-lymphocytes | CD19+ | 0.6 | 161.9 | 0.4 | 5.8 | 131.9 | 4.2 | 224.1 | 0 | 100 |

The results indicated that CD8$^+$ and CD4$^+$ T lymphocytes contain above 99% TpG variant for the CD3 position, while CD19$^+$ B-cells, CD15+ granulocytes, CD14$^+$ monocytes and CD3$^-$ CD56$^+$ natural killer cells contain below 1% of the TpG variant and consist exclusively of the CpG variant. When an equivalent analysis was performed at the GNLY region, more than 95% of the TpG variant was observed for both CD3$^-$CD56$^+$ NK and CD3$^+$ CD56$^+$ NKT cells. CD19$^+$ B-cells, CD15$^+$ granulocytes, CD14$^+$ monocytes consist exclusively of the CpG variant. 2.6% of CD4$^+$ cells and 20.6% of CD8 memory T cells were detected as TpG variant for the GNLY locus.

Finally, the GAPDH gene region was tested for bisulfite-conversion accessibility in all named cell types. Here, specific amplification of the CpG variant failed completely in all tissues and cell types. This is consistent with the bisulphite sequencing data and the notion that this region must always be fully transcriptionally active. The data showed an efficient amplification of the TpG DNA variant for GAPDH in purified cell types (Table 1). The inventors therefore assume that this gene is optimally suitable for determination of the whole cell count in any given sample, measuring a biologically required, fully unmodified DNA stretch for controlling cell numbers.

Based on these data, the inventors intended to further prove the technical accuracy of the various qPCR systems. To do so, FACS purified regulatory T cells were selected, whose bisulfite converted DNA was shown to consist of 99.9% of the TpG variant in the CD3 locus. Granulocytes were shown to be completely inaccessible to bisulfite conversion and consisted to 99.7% of the CpG variant in the CD3 analyses. Then 40, 20, 10, 5, 3, 2 and 1% of CD3 positive regulatory T cells were spiked into a background of granulocytes, and the share of TpG variant at the CD3 locus in the background of the CpG variant was determined. As shown in Table 2, a strict correlation between the spiked samples and the CD3 PCR measurements (Pearson r=0.998) was found, corresponding with the strict correlation that was observed for the FOXP3 PCR (Pearson r=0.998) used as control comparison. The spiking experiment was performed using the GNLY assay, using purified CD3$^-$CD56$^+$ NK cells as TpG variant and granulocytes as CpG variant. As with the CD3 assay, the ratio of TpG variants corresponded well (Pearson r=0.98) to the expected ratios from the spiking experiment (Table 2).

surement with the proportion of TpG DNA found for the Foxp3 locus showed a strong and statistically highly significant correlation (R=0.84, p=2.13E-5). The ratio of Foxp3 to CD3 cells measured by either FACS or epigenetic analysis were also strongly correlated (R=0.7, p=0.00098). The inventors thus found a lower, but solid correlation between flow cytometrically measured CD3$^-$CD56$^+$ and CD3+CD56$^+$ (NK and NKT) cells to the ratio of the TpG variant found in the granulysin locus (R=0.59, p=0.006).

QPCR Analysis of Foxp3 TSDR, CD3 and Granulysin in Solid Tumours

To provide a fully quantitative evaluation of tissue-infiltrating Foxp3$^+$ Tregs, CD3$^+$ T-lymphocytes and granulysin positive cytotoxic cells in healthy tissue and tumour microenvironment, fresh frozen ovarian cancer samples (n=86) were compared with healthy ovarian tissue and benign cysts (n=15) from independent donors. A statistically significant (p=2.34E-11) increase of Foxp3$^+$ cells in the tumour (median: 1.28%) compared to healthy controls (0.12%) was observed. Furthermore, the inventors observed a higher amount of CD3$^+$ T cells in the tumour (median: 7.76%, n=84) than in healthy tissue (4.27%, n=15). This increase was statistically significant with p=2.56E-7. For the ratio between Foxp3$^+$ Tregs and the overall T lymphocyte

TABLE 2

| Target cells | FOXP3-Assay | | CD3-Assay | | GNLY-Assay | |
|---|---|---|---|---|---|---|
| spiked in [%] | TpG/TpG + CpG | TpG/TpG GAPDH/ | TpG/TpG + CpG | TpG/TpG GAPDH/ | TpG/TpG + CpG | TpG/TpG GAPDH/ |
| 0 | 0 | 0 | 0.6 | 0.9 | 0.1 | 0.1 |
| 1 | 1 | 1.4 | 1.4 | 1.7 | 0.4 | 0.3 |
| 2 | 1.7 | 2.5 | 2.5 | 3 | 0.6 | 0.5 |
| 3 | 2.6 | 3.9 | 3.6 | 4.5 | 0.6 | 0.5 |
| 5 | 4.3 | 6.1 | 5.9 | 6.9 | 1.5 | 1.1 |
| 10 | 8.7 | 12.2 | 11.4 | 13.4 | 3.1 | 2 |
| 20 | 20.5 | 25.8 | 22.1 | 26.5 | 5.6 | 4.2 |
| 40 | 37.2 | 46.5 | 42.4 | 47.8 | 13.6 | 9.3 |
| Pearson Correl. Coeff. [r] | 0.9985 | 0.9987 | 0.9998 | 0.9989 | 0.9958 | 0.9979 |

Next, a plasmid was designed that contained sequences corresponding to the TpG versions of the regions in CD3, FOXP3, GNLY and GAPDH (FIG. 3). This construct is considered as the ultimate standard for quantification as it harbours all target regions in an equimolar stoichometry. Using this plasmid for normalization, the relative amount of CD3, FOXP3 and GNLY TpG variants compared to the overall cell count as determined by GAPDH TpG variant (Table 2) was re-quantified. It was shown that the results are in very good agreement with the quantification by the internal standard as well as the original dilution of the cells.

Analysis of Treg, General T Lymphocytes and NK Cells in Whole Blood Samples Applying Epigenetic qPCR In order to test the applicability of this method, the inventors tested whole blood samples from ovarian cancer patients that were enrolled in a catumaxumab trial, and compared the results with data obtained from flow cytometric analysis. The proportion of CD3$^+$ cells as determined by FACS analysis and the proportion of the TpG variant as determined by CD3 qPCR, the inventors showed Spearman rank correlation and high statistical significance (R=0.80; p=7.25E-5) (Table 2). Similarly, comparison of the proportion of CD4$^+$CD25$^+$Cd127$^-$ cells obtained from FACS meacount, the inventors observed a median change from 3.38% Treg of the overall T cell count in healthy tissue (n=15) to app. 19.7% in tumour tissue (n=84) (p=8.06E-07). No meaningful changes were observed for granulysin expressing cells. For bronchial carcinoma (BC), the inventors were able to compare formalin fixed, paraffin embedded (FFPE) patient-matched healthy and tumour samples. The inventors observed a strong increase of Tregs in tumour (median: 4.2%) compared to healthy tissue (mean: 2.0%). This increase was statistically highly significant for both pairwise (n=52, p=2.76E-2) and non-pairwise (n$_{healthy}$=52, n$_{tumour}$=91, p=9.14E-3) comparison. Here, the inventors observed a pronounced decrease of CD3 T lymphocytes in tumour (median: 22.3%) compared to normal tissue (median: 29.6%). This change was statistically significant in both pairwise (n=76, p=3.36E-3) and non-pairwise (n$_{tumour}$=87, n$_{healthy}$=76, p=3.4E-3) analysis. The ratio of Treg to overall CD3 cells was increased in the tumour (median: 18.3%) compared to healthy samples (median: 7.6%). This change was statistically significant in pairwise (n=48, p=6.35E-11) and non-pairwise comparisons (n$_{tumour}$=86, n$_{healthy}$=48, p=1.59E-14). The inventors also tested granulysin positive cells and found a pronounced decrease of these cells in tumour (median: 1.9%) compared to healthy (median: 4.8%) tissues. This difference is statistically significant, both in pairwise ($n_{tumour}$=89 $n_{normal}$=46, p=1.59E-14) and in unpaired comparisons (n=46, p=9.77E-9). Finally, the inventors analysed the same epigenetic parameters in colorectal cancer (CRC) samples and their adjacent healthy control tissue. The inventors observed a statistically highly significant increase of Treg counts in tumour (median: 4.2%) versus healthy (median: 1.78%) tissue (pairwise comparison: n=49, p=6.29E-4; unpaired: $n_{tumour}$=49, $n_{healthy}$=52, p=5.9E-4). The inventors also found a statistically significant reduction of the median overall T lymphocyte count, which was at 24.9% in the tumour and 32.3% in healthy tissue (pairwise comparison: n=61, p=2.59E-2; unpaired: $n_{tumour}$=61, $n_{healthy}$=69, p=2.75E-2). The median increase of the Treg to overall T-lymphocyte was highly significant (pairwise comparison: n=49, p=4.75E-7; unpaired: $n_{tumour}$=52, $n_{healthy}$=49, p=5.1E-7). In healthy tissue, the median number of Tregs in T-lymphocytes is at 7.8%, while in CRC tissue this ratio jumps up to 21.8%. The inventors also tested granulysin as a marker for cytotoxic immune cells, and the inventors observed a trend-wise decrease of granulysin positive cells, with a median of 2.31% GNLY+ cells in tumour versus 3.0% in healthy tissue. This trend, however, was not statistically significant (pairwise comparison: n=50, p=8.43E-2; unpaired: $n_{tumour}$=50, $n_{healthy}$=58, p=8.04E-2).

Since Tregs are also CD3 positive, the inventors wanted to understand if there is a correlation between Foxp3 to CD3 cells in blood and healthy and tumour tissue. With not sufficient healthy ovarian tissue available for this analysis, the inventors find Spearman rank correlation rho equaling 0.47 (p=0.000, N=124), 0.68 (p=0.000, N=48) and 0.55 (p=0.000, N=49) for healthy blood, lung and colorectal tissue respectively (Table 3) between Foxp3 and CD3 TpG. Similarly, the inventors observe a correlation of rho=0.48 (p=0.000, N=86), 0.325 (p=0.325, p=0.019) and 0.76 (p=0.000, N=107) for bronchial, colorectal and ovarian cancers. According to the inventors' findings, the number of cells with an accessible granulysin locus does not significantly correlate to patient prognosis. The inventors thus conclude that the amount of regulatory T cells in the tumour microenvironment depends on the number of overall CD3 cells.

Correlating Disease Prognosis with Intra-tumoral Immune Cell Counts

For colorectal and ovarian cancer patients follow-up data were available. Hence, the inventors tested if the measured immune cell counts within tumour microenvironment at diagnosis and surgery correlated with the prognosis of the patients. In agreement with data shown by Gallon et al., the inventors observed a statistically significant survival advantage for patients with high compared to low CD3 counts in colorectal cancer patients. For this analysis, the inventors distributed patients in two groups, one containing patients with CD3 counts below the median of 23.9% CD3 cells and the other with CD3 counts above the median. A mean survival of 75-99 months compared to 50-73 months in the 95% confidence interval and a hazard ratio of 0.58 was observed. Survival analysis for ovarian cancer patients yielded a strong, but statistically non-significant trend towards better survival for patients within the group with high CD3 counts (above 7.76%) versus those with a lower CD3 count (below 7.76%). The inventors' data indicate a statistically non-significant association of increasing Treg numbers with improved survival. Instead, the inventors show a direct linear correlation between Treg numbers and overall CD3 cell count.

The invention claimed is:

1. A method for identifying a T lymphocyte in a sample of cells obtained from a mammal, the method comprising:
   a) quantifying an amount of accessible chromatin in regions of a CD3 gene in the genome of said cells by bisulfite treatment and quantitative polymerase chain reaction (qPCR);
   b) quantifying an amount of accessible chromatin in regions of a housekeeping gene by bisulfite treatment and qPCR;
   c) carrying out a first step of normalizing said amount of accessible chromatin in said CD3 gene and said housekeeping gene to a known number of copies of a plasmid containing sequences equivalent to bisulfite-converted methylated versions of said CD3 regions and said housekeeping regions;
   d) carrying out a second step of normalizing said amount of accessible chromatin in said CD3 gene and said housekeeping gene to a known number of copies of a plasmid containing sequences equivalent to bisulfite-converted non-methylated versions of said CD3 regions and said housekeeping regions; and
   e) concluding the presence or absence of a T lymphocyte in said sample based on said first and second steps of normalizing.

2. The method according to claim 1, wherein said concluding further comprises a quantification of the cells based on said amounts of accessible chromatin in said regions as determined.

3. The method according to claim 1, wherein said housekeeping gene is selected from a gene encoding actin, glyceraldehyde 3-phosphate dehydrogenase (GAPDH), aldolase, hexokinase, and cyclophilin.

4. The method, according to claim 3, wherein said housekeeping gene is GAPDH.

5. The method according to claim 1, wherein the sample is selected from the group consisting of blood or fractions thereof, saliva, buccal, tears, semen, urine, sweat, faecal material, skin and hair.

* * * * *